(12) United States Patent
Feucht et al.

(10) Patent No.: US 7,615,514 B2
(45) Date of Patent: *Nov. 10, 2009

(54) SELECTIVE HERBICIDES BASED ON SUBSTITUTED ARYLSULPHONYLAMINOCARBONYL-TRIAZOLINONES AND SAFENERS

(75) Inventors: Dieter Feucht, Monheim (DE); Peter Dahmen, Neuss (DE); Mark Wilhelm Drewes, Langenfeld (DE); Rolf Pontzen, Leichlingen (DE); Klaus-Helmut Müller, Düsseldorf (DE); Hans-Georg Schwarz, Langenfeld (DE)

(73) Assignee: Bayer CropScience AG, Monheim (DE)

(*) Notice: Subject to any disclaimer, the term of this patent is extended or adjusted under 35 U.S.C. 154(b) by 0 days.

This patent is subject to a terminal disclaimer.

(21) Appl. No.: 10/488,037

(22) PCT Filed: Aug. 21, 2002

(86) PCT No.: PCT/EP02/09329

§ 371 (c)(1),
(2), (4) Date: Aug. 6, 2004

(87) PCT Pub. No.: WO03/020692

PCT Pub. Date: Mar. 13, 2003

(65) Prior Publication Data

US 2006/0234864 A1    Oct. 19, 2006

(30) Foreign Application Priority Data

Sep. 3, 2001    (DE) ................... 101 43 083

(51) Int. Cl.
*A01N 25/32* (2006.01)
*A01N 43/653* (2006.01)
*A01N 41/06* (2006.01)
(52) U.S. Cl. ............... 504/112; 504/139; 504/149
(58) Field of Classification Search .............. 504/111, 504/112
See application file for complete search history.

(56) References Cited

U.S. PATENT DOCUMENTS

| | | | | |
|---|---|---|---|---|
| 5,057,144 A | 10/1991 | Daum et al. | ............... | 71/92 |
| 5,085,684 A | 2/1992 | Müller et al. | ............... | 71/92 |
| 5,094,683 A | 3/1992 | Daum et al. | ............... | 71/94 |
| 5,149,356 A | 9/1992 | Müller et al. | ............... | 71/90 |
| 5,241,074 A | 8/1993 | Daum et al. | ............... | 548/263.8 |
| 5,276,162 A | 1/1994 | Müller et al. | ............... | 548/263.4 |
| 5,300,480 A | 4/1994 | Haas et al. | ............... | 504/273 |
| 5,380,863 A | 1/1995 | Muller et al. | ............... | 548/263.6 |
| 5,405,970 A | 4/1995 | Daum et al. | ............... | 548/263.6 |
| 5,488,028 A | 1/1996 | Haas et al. | ............... | 504/193 |
| 5,532,378 A | 7/1996 | Daum et al. | ............... | 548/263.8 |
| 5,541,337 A | 7/1996 | Müller et al. | ............... | 548/263.6 |
| 5,554,761 A | 9/1996 | Haas et al. | ............... | 548/263.6 |
| 5,597,939 A * | 1/1997 | M uller et al. | ............... | 558/8 |
| 5,599,944 A | 2/1997 | Müller et al. | ............... | 548/263.6 |
| 5,625,074 A | 4/1997 | Daum et al. | ............... | 548/263.8 |
| 5,631,380 A | 5/1997 | Haas et al. | ............... | 548/263.4 |
| 5,652,372 A | 7/1997 | Müller et al. | ............... | 548/263.4 |
| 5,750,718 A | 5/1998 | Müller et al. | ............... | 548/263.6 |
| 5,994,273 A | 11/1999 | Müller et al. | ............... | 504/273 |
| 6,121,204 A | 9/2000 | Müller et al. | ............... | 504/273 |
| 6,153,761 A | 11/2000 | Müller et al. | ............... | 548/263.6 |
| 6,162,762 A | 12/2000 | Cornes et al. | ............... | 504/105 |
| 6,235,680 B1 | 5/2001 | Ziemer et al. | ............... | 504/112 |
| 6,251,827 B1 * | 6/2001 | Ziemer et al. | ............... | 504/130 |
| 6,251,831 B1 | 6/2001 | Müller et al. | ............... | 504/273 |
| 6,316,386 B1 | 11/2001 | Dahmen et al. | ............... | 504/128 |
| 6,511,940 B1 | 1/2003 | Ziemer et al. | ............... | 504/118 |
| 6,525,211 B1 | 2/2003 | Müller et al. | ............... | 558/413 |
| 6,649,565 B1 | 11/2003 | Feucht et al. | ............... | 504/105 |
| 6,849,578 B1 * | 2/2005 | Wellmann et al. | ............... | 504/130 |
| 2001/0056040 A1 | 12/2001 | Dahmen et al. | ............... | 504/128 |
| 2003/0171220 A1 | 9/2003 | Ziemer et al. | ............... | 504/271 |
| 2003/0211942 A1 | 11/2003 | Feucht et al. | ............... | 504/130 |
| 2004/0116294 A1 * | 6/2004 | Feucht et al. | ............... | 504/139 |
| 2005/0090397 A1 * | 4/2005 | Feucht et al. | ............... | 504/149 |
| 2005/0192182 A1 * | 9/2005 | Feucht et al. | ............... | 504/136 |

FOREIGN PATENT DOCUMENTS

| | | |
|---|---|---|
| CA | 2201596 | 4/1996 |
| DE | 199 40 859 | 3/2001 |
| EP | 0 931 456 | 7/1999 |

OTHER PUBLICATIONS

CABA abstract 2000:21193 (2000).*
CABA abstract 2000:21114 (2000).*

* cited by examiner

*Primary Examiner*—John Pak
(74) *Attorney, Agent, or Firm*—Richard E. L. Henderson

(57) ABSTRACT

The invention relates to novel selective herbicidal compositions comprising an active compound combination consisting of substituted arylsulphonylaminocarbonyl-triazolinones and/or salts thereof and at least one compound which improves crop plant compatibility from the following group of compounds of the general formula (II),

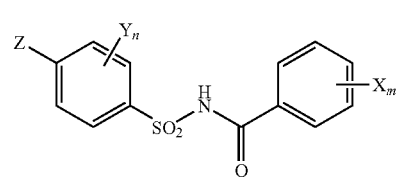

(II)

in which n, m, X, Y and Z are as defined in the disclosure, it being possible to use the compositions with particularly good results for the selective control of weeds in various crops of useful plants. The invention further relates to the use of these compositions for controlling undesirable vegetation.

3 Claims, No Drawings

SELECTIVE HERBICIDES BASED ON SUBSTITUTED ARYLSULPHONYLAMINOCARBONYL-TRIAZOLINONES AND SAFENERS

The present patent application has been filed under 35 U.S.C. 371 as a national stage application of PCT/EP02/09329, filed Aug. 21, 2002, which was published in German as International Patent Publication WO 03/020692 on Mar. 13, 2003, which is entitled to the right of priority of German Patent Application 101 43 083.3, filed Sep. 3, 2001.

The invention relates to novel selective herbicidal active compound combinations comprising substituted arylsulphonylaminocarbonyl-triazolinones and/or salts thereof and at least one compound which improves crop plant compatibility, which combinations can be used with particularly good results for the selective control of weeds in various crops of useful plants.

Substituted arylsulphonylaminocarbonyl-triazolinones are already known as effective herbicides (cf. EP-A-341489, EP-A-422469, EP-A-425948, EP-A-431291, EP-A-507171, EP-A-534266, WO-A-96/11188, WO-A-96/27590, WO-A-96/27591, WO-A-97/03056). However, the activity of these compounds and/or their compatibility with crop plants are not under all conditions entirely satisfactory.

Also known are combinations of substituted arylsulphonylaminocarbonyl-triazolinones and other herbicidally active compounds to obtain a synergistic effect (cf. WO-A-98/12923). Combinations of substituted arylsulphonylaminocarbonyl-triazolinones and safeners, too, are already known (cf. DE-A-19940859, DE-A-19940860, U.S. Pat. No. 6,162,762). However, in these combination products, too, the use properties are not under all conditions entirely satisfactory. Furthermore, combinations of substituted arylsulphonylaminocarbonyl-triazolinones and further herbicidally active compounds, if appropriate with the additional use of safeners, also form part of the subject-matter of an earlier, but not prior published patent application (cf. DE-A-10031825 dated 30, Jun. 2000).

Surprisingly, it has now been found that certain substituted arylsulphonylaminocarbonyl-triazolinones, when used together with the crop-plant-compatibility-improving compounds (safeners/antidotes) described below, prevent damage to the crop plants extremely well and can be used particularly advantageously as broad-spectrum combination preparations for the selective control of weeds in crops of useful plants, such as, for example, in cereals, maize and rice.

The invention provides selective herbicidal compositions, characterized by an effective amount of an active compound combination comprising (a) one or more substituted arylsulphonylaminocarbonyl-triazolinones of the formula (I)

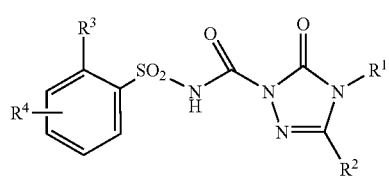

(I)

in which $R^1$ represents hydrogen, hydroxyl, amino, $C_2$-$C_6$-alkylideneamino, represents in each case optionally cyano-, halogen- or $C_1$-$C_4$-alkoxy-substituted alkyl, alkenyl, alkynyl, alkoxy, alkenyloxy, alkylamino or dialkylamino having in each case up to 6 carbon atoms, represents in each case optionally cyano-, halogen- or $C_1$-$C_4$-alkyl-substituted cycloalkyl, cycloalkylalkyl or cycloalkylamino having in each case 3 to 6 carbon atoms in the cycloalkyl group and, if appropriate, 1 to 4 carbon atoms in the alkyl moiety, or represents in each case optionally cyano-, nitro-, halogen-, $C_1$-$C_4$-alkyl-, $C_1$-$C_4$-haloalkyl-, $C_1$-$C_4$-alkoxy- or $C_1$-$C_4$-haloalkoxy-substituted phenyl or phenyl-$C_1$-$C_4$-alkyl, $R^2$ represents hydrogen, hydroxyl, mercapto, amino, cyano, halogen, represents in each case optionally cyano-, halogen- or $C_1$-$C_4$-alkoxy-substituted alkyl, alkoxy, alkylthio, alkylamino, dialkylamino, alkenyl, alkynyl, alkenyloxy, alkynyloxy, alkenylthio, alkynylthio, alkenylamino or alkynylamino having in each case up to 6 carbon atoms, represents in each case optionally cyano-, halogen- or $C_1$-$C_4$-alkyl-substituted cycloalkyl, cycloalkyloxy, cycloalkylthio, cycloalkylamino, cycloalkylalkyl, cycloalkylalkoxy, cycloalkylalkylthio or cycloalkylalkylamino having in each case 3 to 6 carbon atoms in the cycloalkyl group and, if appropriate, 1 to 4 carbon atoms in the alkyl moiety, or represents in each case optionally cyano-, nitro-, halogen-, $C_1$-$C_4$-alkyl-, $C_1$-$C_4$-haloalkyl-, $C_1$-$C_4$-alkoxy- or $C_1$-$C_4$-haloalkoxy-substituted phenyl, phenoxy, phenylthio, phenylamino or phenyl-$C_1$-$C_4$-alkyl, $R^3$ represents nitro, cyano, halogen, represents in each case optionally cyano-, halogen- or $C_1$-$C_4$-alkoxy-substituted alkyl, alkylcarbonyl, alkoxy, alkoxycarbonyl, alkylthio, alkylsulphinyl, alkylsulphonyl, alkylamino, alkenyl, alkenyloxy, alkenylthio, alkenylamino, alkynyl, alkynyloxy, alkynylthio having in each case up to 6 carbon atoms, represents in each case optionally cyano-, halogen- or $C_1$-$C_4$-alkyl-substituted cycloalkyl, cycloalkyloxy, cycloalkylthio, cycloalkylamino having in each case 3 to 6 carbon atoms in the cycloalkyl groups, or represents in each case optionally cyano-, nitro-, halogen-, $C_1$-$C_4$-alkyl-, $C_1$-$C_4$-haloalkyl-, $C_1$-$C_4$-alkoxy- or $C_1$-$C_4$-haloalkoxy-substituted phenyl, phenoxy, phenylthio, phenylsulphinyl, phenylsulphonyl or phenylamino, and $R^4$ represents hydrogen, nitro, cyano, halogen, represents in each case optionally cyano-, halogen- or $C_1$-$C_4$-alkoxy-substituted alkyl, alkylcarbonyl, alkoxy, alkoxycarbonyl, alkylthio, alkylsulphinyl, alkylsulphonyl, alkylamino, alkenyl, alkenyloxy, alkenylthio, alkenylamino, alkynyl, alkynyloxy or alkynylthio having in each case up to 6 carbon atoms, represents in each case optionally cyano-, halogen- or $C_1$-$C_4$-alkyl-substituted cycloalkyl, cycloalkyloxy, cycloalkylthio, cycloalkylamino having in each case 3 to 6 carbon atoms in the cycloalkyl groups, or represents in each case optionally cyano-, nitro-, halogen-, $C_1$-$C_4$-alkyl-, $C_1$-$C_4$-haloalkyl-, $C_1$-$C_4$-alkoxy- or $C_1$-$C_4$-haloalkoxy-substituted phenyl, phenoxy, phenylthio, phenylsulphinyl, phenylsulphonyl or phenylamino, including all possible tautomeric forms of the compounds of the general formula (I) and salts formed by compounds of the general formula (I) and basic compounds ("active compounds of group 1")

and (b) at least one compound which improves crop plant compatibility, from the group of compounds of the general formula (II) below

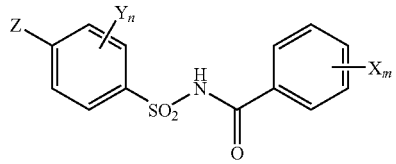

(II)

in which
m represents the numbers 0 to 5,
n represents the numbers 0 to 4,
X represents nitro, cyano, carboxyl, carbamoyl, formyl, sulfamoyl, hydroxyl, amino, halogen, or represents in each case optionally cyano-, halogen- or $C_1$-$C_4$-alkoxy-substituted alkyl, alkoxy, alkoxycarbonyl, alkylthio, alkylsulphinyl, alkylsulphonyl, alkylamino, alkylaminocarbonyl having in each case 1 to 6 carbon atoms in the alkyl groups, or represents dialkylamino, dialkylaminocarbonyl or dialkylaminosulphonyl having in each case 1 to 6 carbon atoms in the alkyl groups,
Y represents nitro, cyano, carboxyl, carbamoyl, formyl, sulfamoyl, hydroxyl, amino, halogen, or represents in each case optionally cyano-, halogen- or $C_1$-$C_4$-alkoxy-substituted alkyl or alkoxy having in each case 1 to 6 carbon atoms, and
Z represents one of the groupings below

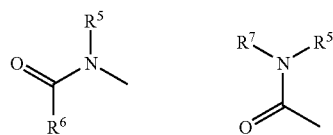

in which
$R^5$ represents hydrogen, represents optionally cyano-, halogen- or $C_1$-$C_4$-alkoxy-substituted alkyl having 1 to 6 carbon atoms, represents in each case optionally halogen-substituted alkenyl or alkynyl having in each case 3 to 6 carbon atoms, or represents in each case optionally halogen- or $C_1$-$C_4$-alkyl-substituted cycloalkyl or cycloalkylalkyl having in each case 3 to 6 carbon atoms in the cycloalkyl group and, if appropriate, 1 to 4 carbon atoms in the alkyl moiety,
$R^6$ represents hydrogen, represents in each case optionally cyano-, halogen-, $C_1$-$C_4$-alkoxy- or $C_1$-$C_4$-alkylthio-substituted alkyl, alkoxy or alkylthio having in each case 1 to 6 carbon atoms, represents in each case optionally halogen-substituted alkenyl, alkenyloxy, alkenylthio, alkynyl, alkynyloxy or alkynylthio having in each case up to 6 carbon atoms, represents in each case optionally halogen- or $C_1$-$C_4$-alkyl-substituted cycloalkyl or cycloalkylalkyl having in each case 3 to 6 carbon atoms in the cycloalkyl group and, if appropriate, 1 to 4 carbon atoms in the alkyl moiety, represents in each case optionally nitro-, cyano-, halogen-, $C_1$-$C_4$-alkyl-, $C_1$-$C_4$-haloalkyl-, $C_1$-$C_4$-alkoxy- or $C_1$-$C_4$-haloalkoxy-substituted aryl, aryloxy, arylalkyl, arylalkoxy or arylalkylthio having in each case 6 or 10 carbon atoms in the aryl group and, if appropriate, 1 to 4 carbon atoms in the alkyl moiety, or represents in each case optionally nitro-, cyano-, halogen-, $C_1$-$C_4$-alkyl-, $C_1$-$C_4$-haloalkyl-, $C_1$-$C_4$-alkoxy- or $C_1$-$C_4$-haloalkoxy-substituted heterocyclyl, heterocyclyloxy, heterocyclylthio, heterocyclylalkyl, heterocyclylalkoxy or heterocyclylalkylthio having in each case up to 10 carbon atoms, 1 to 4 nitrogen atoms and/or 1 or 2 oxygen or sulphur atoms in the heterocyclyl group and, if appropriate, 1 to 4 carbon atoms in the alkyl moiety, and $R^7$ represents hydrogen, represents optionally cyano-, halogen- or $C_1$-$C_4$-alkoxy-substituted alkyl having 1 to 6 carbon atoms, represents alkoxy having 1 to 6 carbon atoms, represents in each case optionally halogen-substituted alkenyl or alkynyl having in each case 3 to 6 carbon atoms, represents alkenyloxy having 3 to 6 carbon atoms, represents in each case optionally halogen- or $C_1$-$C_4$-alkyl-substituted cycloalkyl or cycloalkylalkyl having 3 to 6 carbon atoms in the cycloalkyl group and, if appropriate, 1 to 4 carbon atoms in the alkyl moiety, or represents in each case optionally nitro-, cyano-, halogen-, $C_1$-$C_4$-alkyl-, $C_1$-$C_4$-haloalkyl-, $C_1$-$C_4$-alkoxy- or $C_1$-$C_4$-haloalkoxy-substituted aryl or arylalkyl having in each case 6 or 10 carbon atoms in the aryl group and, if appropriate, 1 to 4 carbon atoms in the alkyl moiety, or together with $R^5$ represents in each case optionally $C_1$-$C_4$-alkyl-substituted alkanediyl having 2 to 6 carbon atoms or oxaalkanediyl having 2 to 5 carbon atoms ("active compounds of group 2").

In the definitions, the hydrocarbon chains, such as in alkyl or alkanediyl, are in each case straight-chain or branched—including in combination with heteroatoms, such as in alkoxy.

Preferred meanings of the groups listed above in connection with the general formula (I) are defined below.

$R^1$ preferably represents hydrogen, amino, propylideneamino, butylideneamino, represents in each case optionally cyano-, fluorine-, chlorine-, methoxy- or ethoxy-substituted methyl, ethyl, n- or i-propyl, n-, i-, s- or t-butyl, ethenyl, propenyl, butenyl, ethynyl, propynyl, butynyl, methoxy, ethoxy, n- or i-propoxy, n-, i-, s- or t-butoxy, propenyloxy, butenyloxy, methylamino, ethylamino, n- or i-propylamino, n-, i-, s- or t-butylamino, dimethylamino or diethylamino, represents in each case optionally cyano-, fluorine-, chlorine-, bromine-, methyl-, ethyl-, n- or i-propyl-substituted cyclopropyl, cyclobutyl, cyclopentyl, cyclohexyl, cyclopropylmethyl, cyclobutylmethyl, cyclopentylmethyl, cyclohexylmethyl, cyclopropylamino, cyclobutylamino, cyclopentylamino or cyclohexylamino, or represents in each case optionally cyano-, nitro-, fluorine-, chlorine-, bromine-, methyl-, ethyl-, n- or i-propyl-, n-, i-, s- or t-butyl-, trifluoromethyl-, methoxy-, ethoxy-, difluoromethoxy- or trifluoromethoxy-substituted phenyl or benzyl.

$R^2$ preferably represents hydrogen, hydroxyl, mercapto, amino, cyano, fluorine, chlorine, bromine, represents in each case optionally cyano-, fluorine-, chlorine-, methoxy- or ethoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino, diethylamino, ethenyl, propenyl, butenyl, ethynyl, propynyl, butynyl, propenyloxy, butenyloxy, propynyloxy, butynyloxy, propenylthio, butenylthio, propynylthio, butynylthio, propenylamino, butenylamino, propynylamino or butynylamino, represents in each case optionally cyano-, fluorine-, chlorine-, bromine-, methyl-, ethyl-, n- or i-propyl-substituted cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino, cyclohexylamino, cyclopropylmethyl, cyclobutylmethyl, cyclopentylmethyl, cyclohexylmethyl, cyclopropylmethoxy, cyclobutylmethoxy, cyclopentylmethoxy, cyclohexylmethoxy, cyclopropylmethylthio, cyclobutylmethylthio, cyclopentylmethylthio, cyclohexylmethylthio, cyclopropylmethylamino, cyclobutylmethylamino, cyclopentylmethylamino or cyclohexylmethylamino, or represents in each case optionally cyano-, nitro-, fluorine-, chlorine-, bromine-, methyl-, ethyl-, n- or i-propyl-, n-, i-, s- or t-butyl-, trifluoromethyl-, methoxy-, ethoxy-, difluoromethoxy- or trifluoromethoxy-substituted phenyl, phenoxy, phenylthio, phenylamino or benzyl.

$R^3$ preferably represents nitro, cyano, fluorine, chlorine, bromine, represents in each case optionally cyano-, fluorine-, chlorine-, methoxy- or ethoxy-substituted methyl, ethyl, n- or i-propyl, n-, i-, s- or t-butyl, acetyl, propionyl, n- or i-butyroyl, methoxy, ethoxy, n- or i-propoxy, n-, i-, s- or t-butoxy, methoxycarbonyl, ethoxycarbonyl, n- or i-propoxycarbonyl, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, methylamino, ethylamino, n- or i-propylamino, n-, i-, s- or t-butylamino, ethenyl, propenyl, butenyl, propenyloxy, butenyloxy, propenylthio, butenylthio, propenylamino, butenylamino, ethynyl, propynyl, butynyl, propynyloxy, butynyloxy, propynylthio or butynylthio, represents in each case optionally cyano-, fluorine-, chlorine-, bromine-, methyl-, ethyl-, n- or i-propyl-substituted cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino or cyclohexylamino, or represents in each case optionally cyano-, nitro-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, n-, i-, s- or t-butoxy-, difluoromethoxy- or trifluoromethoxy-substituted phenyl, phenoxy, phenylthio, phenylsulphinyl, phenylsulphonyl or phenylamino.

$R^4$ preferably represents hydrogen, nitro, cyano, fluorine, chlorine, bromine, represents in each case optionally cyano-, fluorine-, chlorine-, methoxy- or ethoxy-substituted methyl, ethyl, n- or i-propyl, n-, i-, s- or t-butyl, acetyl, propionyl, n- or i-butyroyl, methoxy, ethoxy, n- or i-propoxy, n-, i-, s- or t-butoxy, methoxycarbonyl, ethoxycarbonyl, n- or i-propoxycarbonyl, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, methylamino, ethylamino, n- or i-propylamino, n-, i-, s- or t-butylamino, ethenyl, propenyl, butenyl, propenyloxy, butenyloxy, propenylthio, butenylthio, propenylamino, butenylamino, ethynyl, propynyl, butynyl, propynyloxy, butynyloxy, propynylthio or butynylthio, represents in each case optionally cyano-, fluorine-, chlorine-, bromine-, methyl-, ethyl-, n- or i-propyl-substituted cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino or cyclohexylamino, or represents in each case optionally cyano-, nitro-, fluorine-, chlorine-, bromine-, methyl-, ethyl-, n- or i-propyl-, trifluoromethyl-, methoxy-, ethoxy-, n- or i-propoxy-, n-, i-, s- or t-butoxy-, difluoromethoxy- or trifluoromethoxy-substituted phenyl, phenoxy, phenylthio, phenylsulphinyl or phenylamino.

$R^1$ particularly preferably represents hydrogen, amino, represents in each case optionally fluorine-, chlorine-, methoxy- or ethoxy-substituted methyl, ethyl, ethenyl, propenyl, ethynyl, propynyl, methoxy, ethoxy, n- or i-propoxy, methylamino or ethylamino, represents dimethylamino, or represents optionally fluorine-, chlorine- or methyl-substituted cyclopropyl.

$R^2$ particularly preferably represents hydrogen, chlorine, bromine, represents in each case optionally fluorine-, chlorine-, methoxy- or ethoxy-substituted methyl, ethyl, n- or i-propyl, n-, i- or s-butyl, methoxy, ethoxy, n- or i-propoxy, methylthio, ethylthio, n- or i-propylthio, methylamino, ethylamino, n- or i-propylamino, dimethylamino, diethylamino, ethenyl, propenyl, butenyl, ethynyl, propynyl, butynyl, propenyloxy, butenyloxy, propynyloxy, butynyloxy, propenylthio, butenylthio, propynylthio, butynylthio, propenylamino, butenylamino, propynylamino or butynylamino, or represents in each case optionally fluorine-, chlorine- or methyl-substituted cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino, cyclohexylamino, cyclopropylmethyl, cyclobutylmethyl, cyclopentylmethyl, cyclohexylmethyl, cyclopropylmethoxy, cyclobutylmethoxy, cyclopentylmethoxy, cyclohexylmethoxy, cyclopropylmethylthio, cyclobutylmethylthio, cyclopentylmethylthio, cyclohexylmethylthio, cyclopropylmethylamino, cyclobutylmethylamino, cyclopentylmethylamino and cyclohexylmethylamino.

$R^3$ particularly preferably represents nitro, cyano, fluorine, chlorine, bromine, represents in each case optionally fluorine-, chlorine-, methoxy- or ethoxy-substituted methyl, ethyl, n- or i-propyl, methoxy, ethoxy, n- or i-propoxy, methoxycarbonyl, ethoxycarbonyl, n- or i-propoxycarbonyl, methylthio, ethylthio, n- or i-propylthio, methylsulphinyl, ethylsulphinyl, methylsulphonyl or ethylsulphonyl, represents in each case optionally fluorine-, chlorine- or methyl-substituted cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio or cyclohexylthio, or represents in each case optionally cyano-, nitro-, fluorine-, chlorine-, bromine-, methyl-, ethyl-, n- or i-propyl-, n-, i-, s- or t-butyl, trifluoromethyl-, methoxy-, ethoxy-, n- or i-propoxy-, difluoromethoxy- or trifluoromethoxy-substituted phenyl, phenoxy, phenylthio, phenylsulphinyl or phenylsulphonyl.

$R^4$ particularly preferably represents hydrogen, nitro, cyano, fluorine, chlorine, bromine, or represents in each case optionally fluorine-, chlorine-, methoxy- or ethoxy-substituted methyl, ethyl, n- or i-propyl, methoxy, ethoxy, n- or i-propoxy, methoxycarbonyl, ethoxycarbonyl, n- or i-propoxycarbonyl, methylthio, ethylthio, n- or i-propylthio, methylsulphinyl, ethylsulphinyl, methylsulphonyl or ethylsulphonyl.

$R^1$ very particularly preferably represents hydrogen, represents in each case optionally fluorine-, chlorine-, methoxy- or ethoxy-substituted methyl, ethyl, ethenyl, methoxy, ethoxy, methylamino or ethylamino, represents dimethylamino, or represents optionally fluorine-, chlorine- or methyl-substituted cyclopropyl.

$R^2$ very particularly preferably represents hydrogen, chlorine, bromine, represents in each case optionally fluorine-, chlorine-, methoxy- or ethoxy-substituted methyl, ethyl, n- or i-propyl, n-, i- or s-butyl, methoxy, ethoxy, n- or i-propoxy, methylthio, ethylthio, n- or i-propylthio, methylamino, ethylamino, n- or i-propylamino, dimethylamino, diethylamino, ethenyl, propenyl, butenyl, ethynyl, propynyl, butynyl, propenyloxy, butenyloxy, propynyloxy, butynyloxy, propenylthio, butenylthio, propynylthio, butynylthio, or represents in each case optionally fluorine-, chlorine- or methyl-substituted cyclopropyl, cyclopropyloxy, cyclopropylthio, cyclopropylmethyl, cyclopropylmethoxy or cyclopropylmethylthio.

$R^3$ very particularly preferably represents nitro, cyano, fluorine, chlorine, bromine, represents in each case optionally fluorine-, chlorine-, methoxy- or ethoxy-substituted methyl, ethyl, n- or i-propyl, methoxy, ethoxy, n- or i-propoxy, methoxycarbonyl, ethoxycarbonyl, n- or i-propoxycarbonyl, methylthio, ethylthio, n- or i-propylthio, methylsulphinyl, ethylsulphinyl, methylsulphonyl or ethylsulphonyl, or represents in each case optionally cyano-, nitro-, fluorine-, chlorine-, bromine-, methyl-, ethyl-, trifluoromethyl-, methoxy-, ethoxy-, difluoromethoxy- or trifluoromethoxy-substituted phenyl or phenoxy.

$R^4$ very particularly preferably represents hydrogen, nitro, cyano, fluorine, chlorine, bromine, or represents in each case optionally fluorine-, chlorine-, methoxy- or ethoxy-substituted methyl, ethyl, n- or i-propyl, methoxy, ethoxy, n- or i-propoxy, methoxycarbonyl, ethoxycarbonyl, n- or i-propoxycarbonyl, methylthio, ethylthio, n- or i-propylthio, methylsulphinyl, ethylsulphinyl, methylsulphonyl or ethylsulphonyl.

Instead of the pure active compounds of the formula (I), it is also possible to use salts of the compounds of the formula (I) with metals and/or with basic nitrogen compounds in the active compound combinations according to the invention.

Here, preference is given to salts of the compounds of the formula (I) with alkali metals, such as, for example, lithium, sodium, potassium, rubidium or caesium, in particular with sodium or potassium, with alkaline earth metals, such as, for example, magnesium, calcium or barium, in particular with calcium, or with earth metals, such as, for example, aluminium.

Preference is furthermore given to salts of the compounds of the formula (I) with ammonia, with $C_1$-$C_6$-alkyl-amines, such as, for example, with methylamine, ethylamine, n- or i-propylamine, n-, i-, s- or t-butylamine, n-, i-, s- or t-pentylamine, with di-($C_1$-$C_6$-alkyl)-amines, such as, for example, dimethylamine, diethylamine, dipropylamine, diisopropylamine, dibutylamine, diisobutylamine, di-s-butylamine, dipentylamine, diisopentylamine, di-s-pentylamine and dihexylamine, with tri-($C_1$-$C_4$-alkyl)-amines, such as, for example, trimethylamine, triethylamine, tripropylamine, tributylamine and N-ethyldiisopropylamine, with $C_3$-$C_6$-cycloalkylamines, such as, for example, cyclopentylamine or cyclohexylamine, with di-($C_3$-$C_6$-cycloalkyl)-amines, such as, for example, dicyclopentylamine or dicyclohexylamine, with N—$C_1$-$C_4$-alkyl-$C_3$-$C_6$-cycloalkylamines, such as, for example, N-methylcyclopentylamine, N-ethylcyclopentylamine, N-methylcyclohexylamine or N-ethylcyclohexylamine, with N,N-di-($C_1$-$C_4$-alkyl)-$C_3$-$C_6$-cycloalkylamines, such as, for example, N,N-dimethylcyclopentylamine, N,N-diethylcyclopentylamine, N,N-dimethylcyclohexylamine or N,N-diethyl-cyclohexylamine, with N—$C_1$-$C_4$-alkyl-di-($C_3$-$C_6$-cycloalkyl)-amines, such as, for example, N-methyldicyclopentylamine, N-ethyldicyclopentylamine, N-methyldicyclohexylamine or N-ethyldicyclohexylamine, with phenyl-$C_1$-$C_4$-alkylamines, such as, for example, benzylamine, 1-phenylethylamine or 2-phenylethylamine, with N—$C_1$-$C_4$-alkyl-phenyl-$C_1$-$C_4$-alkyl-amines, such as, for example, N-methylbenzylamine or N-ethylbenzylamine, or N,N-di-($C_1$-$C_4$-alkyl)-phenyl-$C_1$-$C_4$-alkyl-amines, such as, for example, N,N-dimethylbenzylamine or N,N-diethylbenzylamine, or with optionally fused and/or $C_1$-$C_4$-alkyl-substituted azines, such as, for example, pyridine, quinoline, 2-methylpyridine, 3-methylpyridine, 4-methylpyridine, 2,4-dimethylpyridine, 2,5-dimethylpyridine, 2,6-dimethylpyridine or 5-ethyl-2-methylpyridine.

Basic compounds which may be mentioned as being suitable for preparing the salts of the compounds of the formula (I) which can be used according to the invention are:

alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or i-propoxide, n-, i-, s- or t-butoxide or potassium methoxide, ethoxide, n- or i-propoxide, n-, i-, s- or t-butoxide.

Examples of suitable mixing partners according to the invention for the compounds of the formula (I) to be used which may be mentioned are:

2-(2-chlorophenylsulphonylaminocarbonyl)-, 2-(2-bromophenylsulphonylaminocarbonyl)-, 2-(2-methylphenylsulphonylaminocarbonyl)-, 2-(2-ethylphenylsulphonylaminocarbonyl)-, 2-(2-n-propylphenylsulphonylaminocarbonyl)-, 2-(2-i-propylphenylsulphonylaminocarbonyl)-, 2-(2-trifluoromethyl-phenylsulphonylaminocarbonyl)-, 2-(2-methoxyphenylsulphonylaminocarbonyl)-, 2-(2-ethoxyphenylsulphonylaminocarbo-nyl)-, 2-(2-n-propoxyphenylsulphonylaminocarbonyl)-, 2-(2-i-propoxyphenylsulphonylaminocarbonyl)-, 2-(2-difluoromethoxyphenylsulphonylaminocarbonyl)-, 2-(2-trifluoromethoxyphenylsulphonylaminocarbonyl)-, 2-(2-methoxycarbonylphenylsulphonylaminocarbonyl)-, 2-(2-ethoxycarbonylphenylsulphonylaminocarbonyl)-, 2-(2-n-propoxycarbonylphenylsulphonylaminocarbonyl)-, 2-(2-i-propoxycarbonylphenylsulphonylaminocarbonyl)- and 2-(2-chloro-6-methylphenylsulphonylaminocarbonyl)-4-methyl-5-methoxy-2,4-dihydro-3H-1,2,4-triazol-3-one, -4-methyl-5-ethoxy-2,4-dihydro-3H-1,2,4-triazol-3-one, -4-methyl-5-n-propoxy-2,4-dihydro-3H-1,2,4-triazol-3-one, -4-methyl-5-i-propoxy-2,4-dihydro-3H-1,2,4-triazol-3-one, -4-methyl-5-trifluoroethoxy-2,4-dihydro-3H-1,2,4-triazol-3-one, -4-methyl-5-methylthio-2,4-dihydro-3H-1,2,4-triazol-3-one, -4-methyl-5-ethylthio-2,4-dihydro-3H-1,2,4-triazol-3-one, -4-methoxy-5-methyl-2,4-dihydro-3H-1,2,4-triazol-3-one, -4-methoxy-5-ethyl-2,4-dihydro-3H-1,2,4-triazol-3-one, -4-methoxy-5-n-propyl-2,4-dihydro-3H-1,2,4-triazol-3-one, -4-cyclopropyl-5-methoxy-2,4-dihydro-3H-1,2,4-triazol-3-one, -4-cyclopropyl-5-ethoxy-2,4-dihydro-3H-1,2,4-triazol-3-one, -4-cyclopropyl-5-n-propoxy-2,4-dihydro- 3H-1,2,4-triazol-3-one, -4-cyclopropyl-5-i-propoxy-2,4-dihydro-3H-1,2,4-triazol-3-one and -4-cyclopropyl-5-trifluoroethoxy-2,4-dihydro-3H-1,2,4-triazol-3-one and the sodium and potassium salts of these compounds.

Particular emphasis as mixing components of the formula (I) is given to the compounds 2-(2-methoxycarbonylphenylsulphonylaminocarbonyl)-4-methyl-5-n-propoxy-2,4-dihydro-3H-1,2,4-triazol-3-one (I-1, propoxycarbazone) and 2-(2-trifluoromethoxyphenylsulphonylaminocarbonyl)-4-methyl-5-methoxy-2,4-dihydro-3H-1,2,4-triazol-3-one (I-2, flucarbazone) and their sodium salts—(I-1-Na salt, propoxycabazone-sodium, and I-2-Na salt, flucarbazone-sodium).

The compounds of the formula (I) are described in the patent applications or patents mentioned above.

Preferred meanings of the groups listed above in connection with the general formula (II) are defined below.

m preferably represents the number 0, 1, 2, 3 or 4.

n preferably represents the number 0, 1, 2 or 3.

X preferably represents nitro, cyano, carboxyl, carbamoyl, formyl, sulfamoyl, hydroxy, amino, halogen, represents in each case optionally cyano-, halogen-, methoxy-, ethoxy-, n- or i-propoxy-substituted methyl, ethyl, n- or i-propyl, n-, i-, s- or t-butyl, methoxy, ethoxy, n- or i-propoxy, n-, i-, s- or t-butoxy, methoxycarbonyl, ethoxycarbonyl, n- or i-propoxycarbonyl, n-, i-, s- or t-butoxycarbonyl, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, methylamino, ethylamino, n- or i-propylamino, n-, i-, s- or t-butylamino, methylaminocarbonyl, ethylaminocarbonyl, n- or i-propylaminocarbonyl, or represents dimethylamino, diethylamino, dimethylaminocarbonyl or dimethylaminosulphonyl.

Y preferably represents nitro, cyano, carboxyl, carbamoyl, formyl, sulphamoyl, hydroxyl, amino, halogen, or represents in each case optionally cyano-, halogen-, methoxy-, ethoxy-, n- or i-propoxy-substituted methyl, ethyl, n- or i-propyl, n-, i-, s- or t-butyl, methoxy, ethoxy, n- or i-propoxy, n-, i-, s- or t-butoxy, and Z represents preferably one of the groupings below

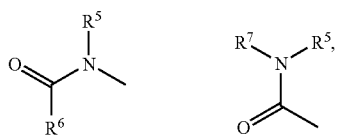

in which

R$^5$ preferably represents hydrogen, represents in each case optionally cyano-, halogen-, methoxy-, ethoxy-, n- or i-propoxy-, n-, i-, s- or t-butoxy-substituted methyl, ethyl, n- or i-propyl, n-, i-, s- or t-butyl, n-, i-, s- or t-pentyl, or neo-pentyl, represents in each case optionally halogen-substituted propenyl, butenyl, pentenyl, propynyl, butynyl or pentynyl, or represents in each case optionally halogen-, methyl-, ethyl-, n- or i-propyl-substituted cyclopropyl, cyclobutyl, cyclopentyl, cyclohexyl, cyclopropylmethyl, cyclobutylmethyl, cyclopentylmethyl or cyclohexylmethyl, R$^6$ preferably represents hydrogen, represents in each case optionally cyano-, halogen-, methoxy-, ethoxy-, n- or i-propoxy-, n-, i-, s- or t-butoxy-, methylthio-, ethylthio-, n- or i-propylthio-, n-, i-, s- or t-butylthio-substituted methyl, ethyl, n- or i-propyl, n-, i-, s- or t-butyl, n-, i-, s- or t-pentyl, or neo-pentyl, methoxy, ethoxy, n- or i-propoxy, n-, i-, s- or t-butoxy, methylthio, ethylthio, n- or i-propylthio, n-, i-, s- or t-butylthio, represents in each case optionally halogen-substituted propenyl, butenyl, pentenyl, propenyloxy, butenyloxy, pentenyloxy, propenylthio, butenylthio, pentenylthio, propynyl, butynyl, pentynyl, propynyloxy, butynyloxy, pentynyloxy, propynylthio, butynylthio or pentynylthio, represents in each case optionally halogen-, methyl-, ethyl-, n- or i-propyl-substituted cyclopropyl, cyclobutyl, cyclopentyl, cyclohexyl, cyclopropylmethyl, cyclobutylmethyl, cyclopentylmethyl or cyclohexylmethyl, represents in each case optionally nitro-, cyano-, halogen-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted phenyl, naphthyl, phenoxy, phenylthio, benzyl, phenylethyl, phenylmethoxy, phenylethoxy or phenylmethylthio, or represents in each case optionally nitro-, cyano-, halogen-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted heterocyclyl, heterocyclyloxy, heterocyclylthio, heterocyclylmethyl, heterocyclylmethoxy or heterocyclylmethylthio, where the heterocyclyl group is preferably selected from the group consisting of furyl, thienyl, pyrazolyl, pyridinyl, pyrimidinyl, R$^7$ preferably represents hydrogen, represents in each case optionally cyano-, halogen-, methoxy-, ethoxy-, n- or i-propoxy-, n-, i-, s- or t-butoxy-substituted methyl, ethyl, n- or i-propyl, n-, i-, s- or t-butyl, n-, i-, s- or t-pentyl, or neo-pentyl, represents methoxy, ethoxy, n- or i-propoxy, n-, i-, s- or t-butoxy, represents in each case optionally halogen-substituted propenyl, butenyl, pentenyl, propynyl, butynyl or pentynyl, represents propenyloxy, butenyloxy or pentenyloxy, represents in each case optionally halogen-, methyl-, ethyl-, n- or i-propyl-substituted cyclopropyl, cyclobutyl, cyclopentyl, cyclohexyl, cyclopropylmethyl, cyclobutylmethyl, cyclopentylmethyl or cyclohexylmethyl, or represents in each case optionally nitro-, cyano-, halogen-, methyl-, ethyl-, n- or i-propyl, n-, i-, s- or t-butyl-, trifluoromethyl-, methoxy-, ethoxy-, n- or i-propoxy-, difluoromethoxy- or trifluoromethoxy-substituted phenyl, naphthyl, benzyl or phenylethyl, or together with R$^5$ represents in each case optionally methyl- or ethyl-substituted butane-1,4-diyl (tetramethylene), 1-oxabutan-1,4-diyl, pentane-1,5-diyl, 1-oxapentane-1,5-diyl or 3-oxapentane-1,5-diyl.

m particularly preferably represents the number 1 or 2.

n particularly preferably represents the number 0.

X particularly preferably represents nitro, cyano, fluorine, chlorine, bromine, represents in each case optionally fluorine-, chlorine-, methoxy- or ethoxy-substituted methyl, ethyl, n- or i-propyl, methoxy, ethoxy, n- or i-propoxy, methoxycarbonyl, ethoxycarbonyl, n- or i-propoxycarbonyl, methylthio, ethylthio, n- or i-propylthio, methylsulphinyl, ethylsulphinyl, methylsulphonyl, ethylsulphonyl, methylamino, ethylamino, n- or i-propylamino, methylaminocarbonyl, ethylaminocarbonyl, n- or i-propylaminocarbonyl, or represents dimethylamino, dimethylaminocarbonyl or dimethylaminosulphonyl.

Z particularly preferably represents one of the groupings below

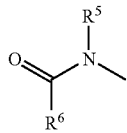 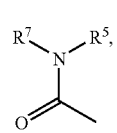

in which

R⁵ particularly preferably represents hydrogen, represents in each case optionally cyano-, fluorine-, chlorine-, methoxy-, ethoxy-, n- or i-propoxy-substituted methyl, ethyl, n- or i-propyl, n- or i-butyl, represents in each case optionally fluorine- and/oder chlorine-substituted propenyl, butenyl, propynyl or butynyl, or represents in each case optionally fluorine-, chlorine-, methyl- or ethyl-substituted cyclopropyl, cyclobutyl, cyclopentyl, cyclohexyl, cyclopropylmethyl, cyclobutylmethyl, cyclopentylmethyl or cyclohexylmethyl, R⁶ particularly preferably represents hydrogen, represents in each case optionally cyano-, fluorine-, chlorine-, bromine-, methoxy-, ethoxy-, n- or i-propoxy-, methylthio-, ethylthio-, n- or i-propylthio-substituted methyl, ethyl, n- or i-propyl, n-, i-, s- or t-butyl, n-, i-, s- or t-pentyl, or neo-pentyl, methoxy, ethoxy, n- or i-propoxy, n-, i-, s- or t-butoxy, methylthio, ethylthio, n- or i-propylthio, n-, i-, s- or t-butylthio, represents in each case optionally fluorine- and/oder chlorine-substituted propenyl, butenyl, pentenyl, propenyloxy, butenyloxy, pentenyloxy, propenylthio, butenylthio, pentenylthio, propynyl, butynyl, pentynyl, propynyloxy, butynyloxy, pentynyloxy, propynylthio, butynylthio or pentynylthio, represents in each case optionally fluorine-, chlorine-, methyl- or ethyl-substituted cyclopropyl, cyclobutyl, cyclopentyl, cyclohexyl, cyclopropylmethyl, cyclobutylmethyl, cyclopentylmethyl or cyclohexylmethyl, represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted phenyl, phenoxy, phenylthio, benzyl, phenylethyl, phenylmethoxy, phenylethoxy or phenylmethylthio, or represents in each case optionally nitro-, cyano-, halogen-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted heterocyclyl, heterocyclyloxy, heterocyclylthio, heterocyclylmethyl, heterocyclylmethoxy or heterocyclylmethylthio, where the heterocyclyl group is preferably selected from the group consisting of furyl, thienyl, pyrazolyl, pyridinyl and pyrimidinyl, and R⁷ particularly preferably represents hydrogen, represents in each case optionally cyano-, fluorine-, chlorine-, methoxy-, ethoxy-, n- or i-propoxy-substituted methyl, ethyl, n- or i-propyl, n-, i-, s- or t-butyl, n-, i-, s- or t-pentyl, or neo-pentyl, represents methoxy, ethoxy, n- or i-propoxy, n-, i-, s- or t-butoxy, represents in each case optionally fluorine- and/oder chlorine-substituted propenyl, butenyl, pentenyl, propynyl, butynyl or pentynyl, represents propenyloxy, butenyloxy or pentenyloxy, represents in each case optionally fluorine-, chlorine-, methyl- or ethyl-substituted cyclopropyl, cyclobutyl, cyclopentyl, cyclohexyl, cyclopropylmethyl, cyclobutylmethyl, cyclopentylmethyl or cyclohexylmethyl, or represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted phenyl, benzyl or phenylethyl, or together with R⁵ represents in each case optionally methyl- or ethyl-substituted butane-1,4-diyl (tetramethylene), 1-oxabutane-1,4-diyl, pentane-1,5-diyl, 1-oxapentane-1,5-diyl or 3-oxapentane-1,5-diyl.

A very particularly preferred group of safeners to be used according to the invention are the compounds of the general formula (IIa)

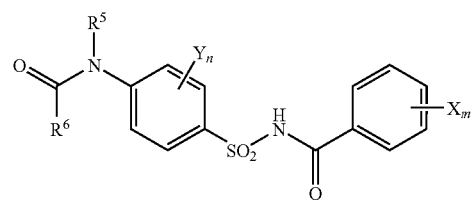

in which m, n, R⁵, R⁶, X and Y have the meanings given above as being preferred or as being particularly preferred.

Examples of the compounds of the formula (IIa) which are very particularly preferred as safeners to be used according to the invention are listed in Table 1 below.

TABLE 1

Examples of compounds of the formula (IIa)

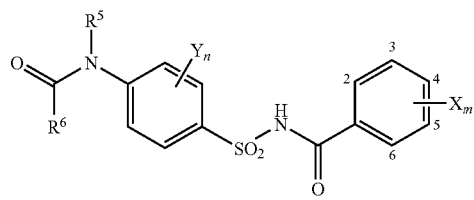

(IIa)

| Ex. No. | R⁵ | R⁶ | (Position/s) $X_m$ | (Position/s) $Y_n$ |
|---------|----|----|--------------------|--------------------|
| IIa-1 | H | H | (2) OCH₃ | — |
| IIa-2 | H | CH₃ | (2) OCH₃ | — |
| IIa-3 | H | CH₃ | (2) OCH₃, (4) Cl | — |
| IIa-4 | H | CH₃ | (2) OCH₃, (4) CH₃ | — |
| IIa-5 | H | CH₃ | (2) OCH₃, (5) Cl | — |
| IIa-6 | H | CH₃ | (2) OCH₃, (4) Cl | — |
| IIa-7 | H | CH₃ | (2) OCH₃, (5) CH₃ | — |
| IIa-8 | H | CH₃ | (2) CF₃ | — |
| IIa-9 | H | CH₃ | (2) OCHF₂ | — |
| IIa-10 | H | CH₃ | (2) OCF₃ | — |
| IIa-11 | H | CH₃ | (2) Cl | — |
| IIa-12 | H | CH₃ | (2) OC₂H₅ | — |
| IIa-13 | H | C₂H₅ | (2) OCH₃ | — |
| IIa-14 | H | C₂H₅ | (2) OCH₃, (4) Cl | — |
| IIa-15 | H | C₂H₅ | (2) OCH₃, (4) CH₃ | — |
| IIa-16 | H | C₂H₅ | (2) OCH₃, (5) Cl | — |
| IIa-17 | H | C₂H₅ | (2) OCH₃, (4) Cl | — |
| IIa-18 | H | C₂H₅ | (2) OCH₃, (5) CH₃ | — |
| IIa-19 | H | C₂H₅ | (2) CF₃ | — |
| IIa-20 | H | C₂H₅ | (2) OCHF₂ | — |
| IIa-21 | H | C₂H₅ | (2) OCF₃ | — |

TABLE 1-continued

Examples of compounds of the formula (IIa)

(IIa)

| Ex. No. | R⁵ | R⁶ | (Position/s) $X_m$ | (Position/s) $Y_n$ |
|---|---|---|---|---|
| IIa-22 | H | C₂H₅ | (2) Cl | — |
| IIa-23 | H | C₂H₅ | (2) OC₂H₅ | — |
| IIa-24 | H | C₃H₇-n | (2) OCH₃ | — |
| IIa-25 | H | C₃H₇-n | (2) OCH₃, (4) Cl | — |
| IIa-26 | H | C₃H₇-n | (2) OCH₃, (4) CH₃ | — |
| IIa-27 | H | C₃H₇-n | (2) OCH₃, (5) Cl | — |
| IIa-28 | H | C₃H₇-n | (2) OCH₃, (4) Cl | — |
| IIa-29 | H | C₃H₇-n | (2) OCH₃, (5) CH₃ | — |
| IIa-30 | H | C₃H₇-n | (2) CF₃ | — |
| IIa-31 | H | C₃H₇-n | (2) OCHF₂ | — |
| IIa-32 | H | C₃H₇-n | (2) OCF₃ | — |
| IIa-33 | H | C₃H₇-n | (2) Cl | — |
| IIa-34 | H | C₃H₇-n | (2) OC₂H₅ | — |
| IIa-35 | H | C₃H₇-i | (2) OCH₃ | — |
| IIa-36 | H | C₃H₇-i | (2) OCH₃, (4) Cl | — |
| IIa-37 | H | C₃H₇-i | (2) OCH₃, (4) CH₃ | — |
| IIa-38 | H | C₃H₇-i | (2) OCH₃, (5) Cl | — |
| IIa-39 | H | C₃H₇-i | (2) OCH₃, (4) Cl | — |
| IIa-40 | H | C₃H₇-i | (2) OCH₃, (5) CH₃ | — |
| IIa-41 | H | C₃H₇-i | (2) CF₃ | — |
| IIa-42 | H | C₃H₇-i | (2) OCHF₂ | — |
| IIa-43 | H | C₃H₇-i | (2) OCF₃ | — |
| IIa-44 | H | C₃H₇-i | (2) Cl | — |
| IIa-45 | H | C₃H₇-i | (2) OC₂H₅ | — |
| IIa-46 | H | cyclopropyl | (2) OCH₃ | — |
| IIa-47 | H | cyclopropyl | (2) OCH₃, (4) Cl | — |
| IIa-48 | H | cyclopropyl | (2) OCH₃, (4) CH₃ | — |
| IIa-49 | H | cyclopropyl | (2) OCH₃, (5) Cl | — |
| IIa-50 | H | cyclopropyl | (2) OCH₃, (4) Cl | — |
| IIa-51 | H | cyclopropyl | (2) OCH₃, (5) CH₃ | — |
| IIa-52 | H | cyclopropyl | (2) CH₃ | — |
| IIa-53 | H | cyclopropyl | (2) CF₃ | — |
| IIa-54 | H | cyclopropyl | (2) OC₂H₅ | — |
| IIa-55 | H | cyclopropyl | (2) Cl | — |
| IIa-56 | H | cyclopropyl | (2) Cl, (5) Cl | — |
| IIa-57 | H | C₄H₉-i | (2) OCH₃ | — |
| IIa-58 | H | C₄H₉-i | (2) OCH₃, (4) Cl | — |
| IIa-59 | H | C₄H₉-i | (2) OCH₃, (4) CH₃ | — |
| IIa-60 | H | C₄H₉-i | (2) OCH₃, (5) Cl | — |
| IIa-61 | H | C₄H₉-i | (2) OCH₃, (4) Cl | — |
| IIa-62 | H | C₄H₉-i | (2) OCH₃, (5) CH₃ | — |
| IIa-63 | H | C₄H₉-i | (2) CF₃ | — |
| IIa-64 | H | C₄H₉-i | (2) OCHF₂ | — |
| IIa-65 | H | C₄H₉-i | (2) OCF₃ | — |
| IIa-66 | H | C₄H₉-i | (2) Cl | — |
| IIa-67 | H | C₄H₉-i | (2) OC₂H₅ | — |
| IIa-68 | H | C₄H₉-s | (2) OCH₃ | — |
| IIa-69 | H | C₄H₉-s | (2) OCH₃, (4) Cl | — |
| IIa-70 | H | C₄H₉-s | (2) OCH₃, (4) CH₃ | — |
| IIa-71 | H | C₄H₉-s | (2) OCH₃, (5) Cl | — |
| IIa-72 | H | C₄H₉-s | (2) OCH₃, (4) Cl | — |
| IIa-73 | H | C₄H₉-s | (2) OCH₃, (5) CH₃ | — |
| IIa-74 | H | C₄H₉-s | (2) CF₃ | — |
| IIa-75 | H | C₄H₉-s | (2) OCHF₂ | — |
| IIa-76 | H | C₄H₉-s | (2) OCF₃ | — |
| IIa-77 | H | C₄H₉-s | (2) Cl | — |
| IIa-78 | H | C₄H₉-s | (2) OC₂H₅ | — |
| IIa-79 | H | C₄H₉-t | (2) OCH₃ | — |
| IIa-80 | H | C₄H₉-t | (2) OCH₃, (4) Cl | — |
| IIa-81 | H | C₄H₉-t | (2) OCH₃, (4) CH₃ | — |
| IIa-82 | H | C₄H₉-t | (2) OCH₃, (5) Cl | — |
| IIa-83 | H | C₄H₉-t | (2) OCH₃, (4) Cl | — |
| IIa-84 | H | C₄H₉-t | (2) OCH₃, (5) CH₃ | — |
| IIa-85 | H | C₄H₉-t | (2) CF₃ | — |
| IIa-86 | H | C₄H₉-t | (2) OCHF₂ | — |
| IIa-87 | H | C₄H₉-t | (2) OCF₃ | — |
| IIa-88 | H | C₄H₉-t | (2) Cl | — |
| IIa-89 | H | C₄H₉-t | (2) OC₂H₅ | — |
| IIa-90 | H | C₄H₉-t | (2) OCH₃ | — |

TABLE 1-continued

Examples of compounds of the formula (IIa)

(IIa)

| Ex. No. | R⁵ | R⁶ | (Position/s) $X_m$ | (Position/s) $Y_n$ |
|---|---|---|---|---|
| IIa-91 | H | cyclobutyl | (2) OCH₃, (4) Cl | — |
| IIa-92 | H | cyclobutyl | (2) OCH₃, (4) CH₃ | — |
| IIa-93 | H | cyclobutyl | (2) OCH₃, (5) Cl | — |
| IIa-94 | H | cyclobutyl | (2) OCH₃, (4) Cl | — |
| IIa-95 | H | cyclobutyl | (2) OCH₃, (5) CH₃ | — |
| IIa-96 | H | cyclobutyl | (2) CF₃ | — |
| IIa-97 | H | cyclobutyl | (2) OCHF₂ | — |
| IIa-98 | H | cyclobutyl | (2) OCF₃ | — |
| IIa-99 | H | cyclobutyl | (2) Cl | — |
| IIa-100 | H | cyclobutyl | (2) OC₂H₅ | — |
| IIa-101 | H | CH₂OCH₃ | (2) OCH₃ | — |
| IIa-102 | H | CH₂OCH₃ | (2) OCH₃, (4) Cl | — |
| IIa-103 | H | CH₂OCH₃ | (2) OCH₃, (4) CH₃ | — |
| IIa-104 | H | CH₂OCH₃ | (2) OCH₃, (5) Cl | — |
| IIa-105 | H | CH₂OCH₃ | (2) OCH₃, (4) Cl | — |
| IIa-106 | H | CH₂OCH₃ | (2) OCH₃, (5) CH₃ | — |
| IIa-107 | H | CH₂OCH₃ | (2) CF₃ | — |
| IIa-108 | H | CH₂OCH₃ | (2) OCHF₂ | — |
| IIa-109 | H | CH₂OCH₃ | (2) OCF₃ | — |
| IIa-110 | H | CH₂OCH₃ | (2) Cl | — |
| IIa-111 | H | CH₂OCH₃ | (2) OC₂H₅ | — |
| IIa-112 | H | CH₂OCH₃ | (2) CH₃ | — |
| IIa-113 | H | CH₂OCH₃ | (2) Cl, (4) Cl | — |
| IIa-114 | H | CH₂OCH₃ | (2) Cl, (5) Cl | — |
| IIa-115 | H | CH₂OCH₃ | (2) OCH₃, (5) OCH₃ | — |
| IIa-116 | H | CH₂OCH₃ | (2) CH₃, (4) CH₃ | — |
| IIa-117 | H | CH₂OCH₃ | (2) CH₃, (5) CH₃ | — |
| IIa-118 | H | CH₂Cl | (2) OCH₃ | — |
| IIa-119 | H | CH₂Cl | (2) OCH₃, (4) Cl | — |
| IIa-120 | H | CH₂Cl | (2) OCH₃, (4) CH₃ | — |
| IIa-121 | H | CH₂Cl | (2) OCH₃, (5) Cl | — |
| IIa-122 | H | CH₂Cl | (2) OCH₃, (4) Cl | — |
| IIa-123 | H | CH₂Cl | (2) OCH₃, (5) CH₃ | — |
| IIa-124 | H | CH₂Cl | (2) CF₃ | — |
| IIa-125 | H | CH₂Cl | (2) OCHF₂ | — |
| IIa-126 | H | CH₂Cl | (2) OCF₃ | — |
| IIa-127 | H | CH₂Cl | (2) Cl | — |
| IIa-128 | H | CH₂Cl | (2) OC₂H₅ | — |
| IIa-129 | H | CH₂Cl | (2) CH₃ | — |
| IIa-130 | H | CH₂Cl | (2) Cl, (4) Cl | — |
| IIa-131 | H | CH₂Cl | (2) Cl, (5) Cl | — |
| IIa-132 | H | CH₂Cl | (2) OCH₃, (5) OCH₃ | — |
| IIa-133 | H | CH₂Cl | (2) CH₃, (4) CH₃ | — |
| IIa-134 | H | CH₂Cl | (2) CH₃, (5) CH₃ | — |
| IIa-135 | H | CHCl₂ | (2) OCH₃ | — |
| IIa-136 | H | CHCl₂ | (2) OCH₃, (4) Cl | — |
| IIa-137 | H | CHCl₂ | (2) OCH₃, (4) CH₃ | — |
| IIa-138 | H | CHCl₂ | (2) OCH₃, (5) Cl | — |
| IIa-139 | H | CHCl₂ | (2) OCH₃, (4) Cl | — |
| IIa-140 | H | CHCl₂ | (2) OCH₃, (5) CH₃ | — |
| IIa-141 | H | CHCl₂ | (2) CF₃ | — |
| IIa-142 | H | CHCl₂ | (2) OCHF₂ | — |
| IIa-143 | H | CHCl₂ | (2) OCF₃ | — |
| IIa-144 | H | CHCl₂ | (2) Cl | — |
| IIa-145 | H | CHCl₂ | (2) OC₂H₅ | — |
| IIa-146 | H | CHCl₂ | (2) CH₃ | — |
| IIa-147 | H | CHCl₂ | (2) Cl, (4) Cl | — |
| IIa-148 | H | CHCl₂ | (2) Cl, (5) Cl | — |
| IIa-149 | H | CHCl₂ | (2) OCH₃, (5) OCH₃ | — |
| IIa-150 | H | CHCl₂ | (2) CH₃, (4) CH₃ | — |
| IIa-151 | H | CHCl₂ | (2) CH₃, (5) CH₃ | — |
| IIa-152 | H | CH₂CH₂Cl | (2) OCH₃ | — |
| IIa-153 | H | CH₂CH₂Cl | (2) OCH₃, (4) Cl | — |
| IIa-154 | H | CH₂CH₂Cl | (2) OCH₃, (4) CH₃ | — |
| IIa-155 | H | CH₂CH₂Cl | (2) OCH₃, (5) Cl | — |
| IIa-156 | H | CH₂CH₂Cl | (2) OCH₃, (4) Cl | — |
| IIa-157 | H | CH₂CH₂Cl | (2) OCH₃, (5) CH₃ | — |
| IIa-158 | H | CH₂CH₂Cl | (2) CF₃ | — |
| IIa-159 | H | CH₂CH₂Cl | (2) OCHF₂ | — |
| IIa-160 | H | CH₂CH₂Cl | (2) OCF₃ | — |
| IIa-161 | H | CH₂CH₂Cl | (2) Cl | — |
| IIa-162 | H | CH₂CH₂Cl | (2) OC₂H₅ | — |

TABLE 1-continued

Examples of compounds of the formula (IIa)

(IIa) — N-substituted sulfonamide with R5, R6 on amide nitrogen attached to phenyl-SO2-NH-C(O)-phenyl(Xm) core; Yn on left phenyl.

| Ex. No. | R5 | R6 | (Position/s) Xm | (Position/s) Yn |
|---|---|---|---|---|
| IIa-163 | H | CH2CH2Cl | (2) CH3 | — |
| IIa-164 | H | CH2CH2Cl | (2) Cl, (4) Cl | — |
| IIa-165 | H | CH2CH2Cl | (2) Cl, (5) Cl | — |
| IIa-166 | H | CH2CH2Cl | (2) OCH3, (5) OCH3 | — |
| IIa-167 | H | CH2CH2Cl | (2) CH3, (4) CH3 | — |
| IIa-168 | H | CH2CH2Cl | (2) CH3, (5) CH3 | — |
| IIa-169 | H | CH2CH2Cl | (2) OCH3 | — |
| IIa-170 | H | 5-methylfuran-2-yl | (2) OCH3, (4) Cl | — |
| IIa-171 | H | 5-methylfuran-2-yl | (2) OCH3, (4) CH3 | — |
| IIa-172 | H | 5-methylfuran-2-yl | (2) OCH3, (5) Cl | — |
| IIa-173 | H | 5-methylfuran-2-yl | (2) OCH3, (4) Cl | — |
| IIa-174 | H | 5-methylfuran-2-yl | (2) OCH3, (5) CH3 | — |
| IIa-175 | H | 5-methylfuran-2-yl | (2) CF3 | — |
| IIa-176 | H | 5-methylfuran-2-yl | (2) OCHF2 | — |
| IIa-177 | H | 5-methylfuran-2-yl | (2) OCF3 | — |
| IIa-178 | H | 5-methylfuran-2-yl | (2) Cl | — |
| IIa-179 | H | 5-methylfuran-2-yl | (2) OC2H5 | — |
| IIa-180 | H | 5-methylfuran-2-yl | (2) CH3 | — |
| IIa-181 | H | 5-methylfuran-2-yl | (2) Cl, (4) Cl | — |
| IIa-182 | H | 5-methylfuran-2-yl | (2) Cl, (5) Cl | — |
| IIa-183 | H | 5-methylfuran-2-yl | (2) OCH3, (5) OCH3 | — |
| IIa-184 | H | 5-methylfuran-2-yl | (2) CH3, (4) CH3 | — |
| IIa-185 | H | 5-methylfuran-2-yl | (2) CH3, (5) CH3 | — |
| IIa-186 | H | OCH3 | (2) OCH3 | — |
| IIa-187 | H | OCH3 | (2) OCH3, (4) Cl | — |
| IIa-188 | H | OCH3 | (2) OCH3, (4) CH3 | — |
| IIa-189 | H | OCH3 | (2) OCH3, (5) Cl | — |

TABLE 1-continued

Examples of compounds of the formula (IIa)

(IIa)

| Ex. No. | R⁵ | R⁶ | (Position/s) X$_m$ | (Position/s) Y$_n$ |
|---|---|---|---|---|
| IIa-190 | H | OCH$_3$ | (2) OCH$_3$, (4) Cl | — |
| IIa-191 | H | OCH$_3$ | (2) OCH$_3$, (5) CH$_3$ | — |
| IIa-192 | H | OCH$_3$ | (2) CF$_3$ | — |
| IIa-193 | H | OCH$_3$ | (2) OCHF$_2$ | — |
| IIa-194 | H | OCH$_3$ | (2) OCF$_3$ | — |
| IIa-195 | H | OCH$_3$ | (2) Cl | — |
| IIa-196 | H | OCH$_3$ | (2) OC$_2$H$_5$ | — |
| IIa-197 | H | OCH$_3$ | (2) CH$_3$ | — |
| IIa-198 | H | OCH$_3$ | (2) Cl, (4) Cl | — |
| IIa-199 | H | OCH$_3$ | (2) Cl, (5) Cl | — |
| IIa-200 | H | OCH$_3$ | (2) OCH$_3$, (5) OCH$_3$ | — |
| IIa-201 | H | OCH$_3$ | (2) CH$_3$, (4) CH$_3$ | — |
| IIa-202 | H | OCH$_3$ | (2) CH$_3$, (5) CH$_3$ | — |
| IIa-203 | H | OC$_2$H$_5$ | (2) OCH$_3$ | — |
| IIa-204 | H | OC$_2$H$_5$ | (2) OCH$_3$, (4) Cl | — |
| IIa-205 | H | OC$_2$H$_5$ | (2) OCH$_3$, (4) CH$_3$ | — |
| IIa-206 | H | OC$_2$H$_5$ | (2) OCH$_3$, (5) Cl | — |
| IIa-207 | H | OC$_2$H$_5$ | (2) OCH$_3$, (4) Cl | — |
| IIa-208 | H | OC$_2$H$_5$ | (2) OCH$_3$, (5) CH$_3$ | — |
| IIa-209 | H | OC$_2$H$_5$ | (2) CF$_3$ | — |
| IIa-210 | H | OC$_2$H$_5$ | (2) OCHF$_2$ | — |
| IIa-211 | H | OC$_2$H$_5$ | (2) OCF$_3$ | — |
| IIa-212 | H | OC$_2$H$_5$ | (2) Cl | — |
| IIa-213 | H | OC$_2$H$_5$ | (2) OC$_2$H$_5$ | — |
| IIa-214 | H | OC$_2$H$_5$ | (2) CH$_3$ | — |
| IIa-215 | H | OC$_2$H$_5$ | (2) Cl, (4) Cl | — |
| IIa-216 | H | OC$_2$H$_5$ | (2) Cl, (5) Cl | — |
| IIa-217 | H | OC$_2$H$_5$ | (2) OCH$_3$, (5) OCH$_3$ | — |
| IIa-218 | H | OC$_2$H$_5$ | (2) CH$_3$, (4) CH$_3$ | — |
| IIa-219 | H | OC$_2$H$_5$ | (2) CH$_3$, (5) CH$_3$ | — |
| IIa-220 | H | OC$_3$H$_7$-n | (2) OCH$_3$ | — |
| IIa-221 | H | OC$_3$H$_7$-n | (2) OCH$_3$, (4) Cl | — |
| IIa-222 | H | OC$_3$H$_7$-n | (2) OCH$_3$, (4) CH$_3$ | — |
| IIa-223 | H | OC$_3$H$_7$-n | (2) OCH$_3$, (5) Cl | — |
| IIa-224 | H | OC$_3$H$_7$-n | (2) OCH$_3$, (4) Cl | — |
| IIa-225 | H | OC$_3$H$_7$-n | (2) OCH$_3$, (5) CH$_3$ | — |
| IIa-226 | H | OC$_3$H$_7$-n | (2) CF$_3$ | — |
| IIa-227 | H | OC$_3$H$_7$-n | (2) OCHF$_2$ | — |
| IIa-228 | H | OC$_3$H$_7$-n | (2) OCF$_3$ | — |
| IIa-229 | H | OC$_3$H$_7$-n | (2) Cl | — |
| IIa-230 | H | OC$_3$H$_7$-n | (2) OC$_2$H$_5$ | — |
| IIa-231 | H | OC$_3$H$_7$-n | (2) CH$_3$ | — |
| IIa-232 | H | OC$_3$H$_7$-n | (2) Cl, (4) Cl | — |
| IIa-233 | H | OC$_3$H$_7$-n | (2) Cl, (5) Cl | — |
| IIa-234 | H | OC$_3$H$_7$-n | (2) OCH$_3$, (5) OCH$_3$ | — |
| IIa-235 | H | OC$_3$H$_7$-n | (2) CH$_3$, (4) CH$_3$ | — |
| IIa-236 | H | OC$_3$H$_7$-n | (2) CH$_3$, (5) CH$_3$ | — |
| IIa-237 | H | OC$_3$H$_7$-i | (2) OCH$_3$ | — |
| IIa-238 | H | OC$_3$H$_7$-i | (2) OCH$_3$, (4) Cl | — |
| IIa-239 | H | OC$_3$H$_7$-i | (2) OCH$_3$, (4) CH$_3$ | — |
| IIa-240 | H | OC$_3$H$_7$-i | (2) OCH$_3$, (5) Cl | — |
| IIa-241 | H | OC$_3$H$_7$-i | (2) OCH$_3$, (4) Cl | — |
| IIa-242 | H | OC$_3$H$_7$-i | (2) OCH$_3$, (5) CH$_3$ | — |
| IIa-243 | H | OC$_3$H$_7$-i | (2) CF$_3$ | — |
| IIa-244 | H | OC$_3$H$_7$-i | (2) OCHF$_2$ | — |
| IIa-245 | H | OC$_3$H$_7$-i | (2) OCF$_3$ | — |
| IIa-246 | H | OC$_3$H$_7$-i | (2) Cl | — |
| IIa-247 | H | OC$_3$H$_7$-i | (2) OC$_2$H$_5$ | — |
| IIa-248 | H | OC$_3$H$_7$-i | (2) CH$_3$ | — |
| IIa-249 | H | OC$_3$H$_7$-i | (2) Cl, (4) Cl | — |
| IIa-250 | H | OC$_3$H$_7$-i | (2) Cl, (5) Cl | — |
| IIa-251 | H | OC$_3$H$_7$-i | (2) OCH$_3$, (5) OCH$_3$ | — |
| IIa-252 | H | OC$_3$H$_7$-i | (2) CH$_3$, (4) CH$_3$ | — |
| IIa-253 | H | OC$_3$H$_7$-i | (2) CH$_3$, (5) CH$_3$ | — |
| IIa-254 | H | OC$_6$H$_5$ | (2) OCH$_3$ | — |
| IIa-255 | H | OC$_6$H$_5$ | (2) OCH$_3$, (4) Cl | — |
| IIa-256 | H | OC$_6$H$_5$ | (2) OCH$_3$, (4) CH$_3$ | — |
| IIa-257 | H | OC$_6$H$_5$ | (2) OCH$_3$, (5) Cl | — |
| IIa-258 | H | OC$_6$H$_5$ | (2) OCH$_3$, (4) Cl | — |
| IIa-259 | H | OC$_6$H$_5$ | (2) OCH$_3$, (5) CH$_3$ | — |
| IIa-260 | H | OC$_6$H$_5$ | (2) CF$_3$ | — |
| IIa-261 | H | OC$_6$H$_5$ | (2) OCHF$_2$ | — |
| IIa-262 | H | OC$_6$H$_5$ | (2) OCF$_3$ | — |
| IIa-263 | H | OC$_6$H$_5$ | (2) Cl | — |
| IIa-264 | H | OC$_6$H$_5$ | (2) OC$_2$H$_5$ | — |
| IIa-265 | H | OC$_6$H$_5$ | (2) CH$_3$ | — |
| IIa-266 | H | OC$_6$H$_5$ | (2) Cl, (4) Cl | — |
| IIa-267 | H | OC$_6$H$_5$ | (2) Cl, (5) Cl | — |
| IIa-268 | H | OC$_6$H$_5$ | (2) OCH$_3$, (5) OCH$_3$ | — |
| IIa-269 | H | OC$_6$H$_5$ | (2) CH$_3$, (4) CH$_3$ | — |
| IIa-270 | H | OC$_6$H$_5$ | (2) CH$_3$, (5) CH$_3$ | — |
| IIa-271 | H | SCH$_3$ | (2) OCH$_3$ | — |
| IIa-272 | H | SCH$_3$ | (2) OCH$_3$, (4) Cl | — |
| IIa-273 | H | SCH$_3$ | (2) OCH$_3$, (4) CH$_3$ | — |
| IIa-274 | H | SCH$_3$ | (2) OCH$_3$, (5) Cl | — |
| IIa-275 | H | SCH$_3$ | (2) OCH$_3$, (4) Cl | — |
| IIa-276 | H | SCH$_3$ | (2) OCH$_3$, (5) CH$_3$ | — |
| IIa-277 | H | SCH$_3$ | (2) CF$_3$ | — |
| IIa-278 | H | SCH$_3$ | (2) OCHF$_2$ | — |
| IIa-279 | H | SCH$_3$ | (2) OCF$_3$ | — |
| IIa-280 | H | SCH$_3$ | (2) Cl | — |
| IIa-281 | H | SCH$_3$ | (2) OC$_2$H$_5$ | — |
| IIa-282 | H | SCH$_3$ | (2) CH$_3$ | — |
| IIa-283 | H | SCH$_3$ | (2) Cl, (4) Cl | — |
| IIa-284 | H | SCH$_3$ | (2) Cl, (5) Cl | — |
| IIa-285 | H | SCH$_3$ | (2) OCH$_3$, (5) OCH$_3$ | — |
| IIa-286 | H | SCH$_3$ | (2) CH$_3$, (4) CH$_3$ | — |
| IIa-287 | H | SCH$_3$ | (2) CH$_3$, (5) CH$_3$ | — |
| IIa-288 | H | SC$_2$H$_5$ | (2) OCH$_3$ | — |
| IIa-289 | H | SC$_2$H$_5$ | (2) OCH$_3$, (4) Cl | — |
| IIa-290 | H | SC$_2$H$_5$ | (2) OCH$_3$, (4) CH$_3$ | — |
| IIa-291 | H | SC$_2$H$_5$ | (2) OCH$_3$, (5) Cl | — |
| IIa-292 | H | SC$_2$H$_5$ | (2) OCH$_3$, (4) Cl | — |
| IIa-293 | H | SC$_2$H$_5$ | (2) OCH$_3$, (5) CH$_3$ | — |
| IIa-294 | H | SC$_2$H$_5$ | (2) CF$_3$ | — |
| IIa-295 | H | SC$_2$H$_5$ | (2) OCHF$_2$ | — |
| IIa-296 | H | SC$_2$H$_5$ | (2) OCF$_3$ | — |
| IIa-297 | H | SC$_2$H$_5$ | (2) Cl | — |
| IIa-298 | H | SC$_2$H$_5$ | (2) OC$_2$H$_5$ | — |
| IIa-299 | H | SC$_2$H$_5$ | (2) CH$_3$ | — |
| IIa-300 | H | SC$_2$H$_5$ | (2) Cl, (4) Cl | — |
| IIa-301 | H | SC$_2$H$_5$ | (2) Cl, (5) Cl | — |
| IIa-302 | H | SC$_2$H$_5$ | (2) OCH$_3$, (5) OCH$_3$ | — |
| IIa-303 | H | SC$_2$H$_5$ | (2) CH$_3$, (4) CH$_3$ | — |
| IIa-304 | H | SC$_2$H$_5$ | (2) CH$_3$, (5) CH$_3$ | — |

A further very particularly preferred group of safeners to be used according to the invention are the compounds of the general formula (IIb)

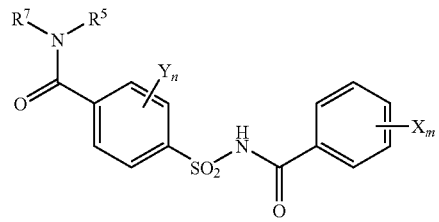

in which m, n, $R^5$, $R^7$, X and Y have the meanings given above as being preferred or as being particularly preferred.

Examples of the compounds of the formula (IIb) which are very particularly preferred as safeners to be used according to the invention are listed in Table 2 below.

TABLE 2

Examples of compounds of the formula (IIb)

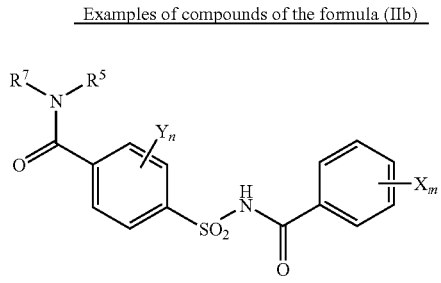

| Ex. No. | $R^5$ | $R^7$ | (Position/s) $X_m$ | (Position/s) $Y_n$ |
|---|---|---|---|---|
| IIb-1 | H | H | (2) $OCH_3$ | — |
| IIb-2 | H | $CH_3$ | (2) $OCH_3$ | — |
| IIb-3 | H | $CH_3$ | (2) $OCH_3$ | — |
| IIb-4 | H | $CH_3$ | (2) $OCH_3$, (4) Cl | — |
| IIb-5 | H | $CH_3$ | (2) $OCH_3$, (4) $CH_3$ | — |
| IIb-6 | H | $CH_3$ | (2) $OCH_3$, (5) Cl | — |
| IIb-7 | H | $CH_3$ | (2) $OCH_3$, (4) Cl | — |
| IIb-8 | H | $CH_3$ | (2) $OCH_3$, (5) $CH_3$ | — |
| IIb-9 | H | $CH_3$ | (2) $CF_3$ | — |
| IIb-10 | H | $CH_3$ | (2) $OCHF_2$ | — |
| IIb-11 | H | $CH_3$ | (2) $OCF_3$ | — |
| IIb-12 | H | $CH_3$ | (2) Cl | — |
| IIb-13 | H | $CH_3$ | (2) $OC_2H_5$ | — |
| IIb-14 | H | $C_2H_5$ | (2) $OCH_3$ | — |
| IIb-15 | H | $C_2H_5$ | (2) $OCH_3$, (4) Cl | — |
| IIb-16 | H | $C_2H_5$ | (2) $OCH_3$, (4) $CH_3$ | — |
| IIb-17 | H | $C_2H_5$ | (2) $OCH_3$, (5) Cl | — |
| IIb-18 | H | $C_2H_5$ | (2) $OCH_3$, (4) Cl | — |
| IIb-19 | H | $C_2H_5$ | (2) $OCH_3$, (5) $CH_3$ | — |
| IIb-20 | H | $C_2H_5$ | (2) $CF_3$ | — |
| IIb-21 | H | $C_2H_5$ | (2) $OCHF_2$ | — |
| IIb-22 | H | $C_2H_5$ | (2) $OCF_3$ | — |
| IIb-23 | H | $C_2H_5$ | (2) Cl | — |
| IIb-24 | H | $C_2H_5$ | (2) $OC_2H_5$ | — |
| IIb-25 | H | $C_2H_5$ | (2) $CH_3$ | — |
| IIb-26 | H | $C_2H_5$ | (2) Cl, (4) Cl | — |
| IIb-27 | H | $C_2H_5$ | (2) Cl, (5) Cl | — |
| IIb-28 | H | $C_2H_5$ | (2) $OCH_3$, (5) $OCH_3$ | — |
| IIb-29 | H | $C_2H_5$ | (2) $CH_3$, (4) $CH_3$ | — |
| IIb-30 | H | $C_2H_5$ | (2) $CH_3$, (5) $CH_3$ | — |
| IIb-31 | H | $C_3H_7$-n | (2) $OCH_3$ | — |
| IIb-32 | H | $C_3H_7$-n | (2) $OCH_3$, (4) Cl | — |
| IIb-33 | H | $C_3H_7$-n | (2) $OCH_3$, (4) $CH_3$ | — |
| IIb-34 | H | $C_3H_7$-n | (2) $OCH_3$, (5) Cl | — |

TABLE 2-continued

Examples of compounds of the formula (IIb)

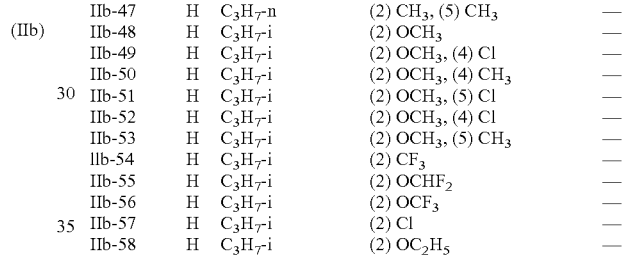

| Ex. No. | $R^5$ | $R^7$ | (Position/s) $X_m$ | (Position/s) $Y_n$ |
|---|---|---|---|---|
| IIb-35 | H | $C_3H_7$-n | (2) $OCH_3$, (4) Cl | — |
| IIb-36 | H | $C_3H_7$-n | (2) $OCH_3$, (5) $CH_3$ | — |
| IIb-37 | H | $C_3H_7$-n | (2) $CF_3$ | — |
| IIb-38 | H | $C_3H_7$-n | (2) $OCHF_2$ | — |
| IIb-39 | H | $C_3H_7$-n | (2) $OCF_3$ | — |
| IIb-40 | H | $C_3H_7$-n | (2) Cl | — |
| IIb-41 | H | $C_3H_7$-n | (2) $OC_2H_5$ | — |
| IIb-42 | H | $C_3H_7$-n | (2) $CH_3$ | — |
| IIb-43 | H | $C_3H_7$-n | (2) Cl, (4) Cl | — |
| IIb-44 | H | $C_3H_7$-n | (2) Cl, (5) Cl | — |
| IIb-45 | H | $C_3H_7$-n | (2) $OCH_3$, (5) $OCH_3$ | — |
| IIb-46 | H | $C_3H_7$-n | (2) $CH_3$, (4) $CH_3$ | — |
| IIb-47 | H | $C_3H_7$-n | (2) $CH_3$, (5) $CH_3$ | — |
| IIb-48 | H | $C_3H_7$-i | (2) $OCH_3$ | — |
| IIb-49 | H | $C_3H_7$-i | (2) $OCH_3$, (4) Cl | — |
| IIb-50 | H | $C_3H_7$-i | (2) $OCH_3$, (4) $CH_3$ | — |
| IIb-51 | H | $C_3H_7$-i | (2) $OCH_3$, (5) Cl | — |
| IIb-52 | H | $C_3H_7$-i | (2) $OCH_3$, (4) Cl | — |
| IIb-53 | H | $C_3H_7$-i | (2) $OCH_3$, (5) $CH_3$ | — |
| IIb-54 | H | $C_3H_7$-i | (2) $CF_3$ | — |
| IIb-55 | H | $C_3H_7$-i | (2) $OCHF_2$ | — |
| IIb-56 | H | $C_3H_7$-i | (2) $OCF_3$ | — |
| IIb-57 | H | $C_3H_7$-i | (2) Cl | — |
| IIb-58 | H | $C_3H_7$-i | (2) $OC_2H_5$ | — |
| IIb-59 | H | $C_3H_7$-i | (2) $CH_3$ | — |
| IIb-60 | H | $C_3H_7$-i | (2) Cl, (4) Cl | — |
| IIb-61 | H | $C_3H_7$-i | (2) Cl, (5) Cl | — |
| IIb-62 | H | $C_3H_7$-i | (2) $OCH_3$, (5) $OCH_3$ | — |
| IIb-63 | H | $C_3H_7$-i | (2) $CH_3$, (4) $CH_3$ | — |
| IIb-64 | H | $C_3H_7$-i | (2) $CH_3$, (5) $CH_3$ | — |
| IIb-65 | H | $CH_2CH=CH_2$ | (2) $OCH_3$ | — |
| IIb-66 | H | $CH_2CH=CH_2$ | (2) $OCH_3$, (4) Cl | — |
| IIb-67 | H | $CH_2CH=CH_2$ | (2) $OCH_3$, (4) $CH_3$ | — |
| IIb-68 | H | $CH_2CH=CH_2$ | (2) $OCH_3$, (5) Cl | — |
| IIb-69 | H | $CH_2CH=CH_2$ | (2) $OCH_3$, (4) Cl | — |
| IIb-70 | H | $CH_2CH=CH_2$ | (2) $OCH_3$, (5) $CH_3$ | — |
| IIb-71 | H | $CH_2CH=CH_2$ | (2) $CF_3$ | — |
| IIb-72 | H | $CH_2CH=CH_2$ | (2) $OCHF_2$ | — |
| IIb-73 | H | $CH_2CH=CH_2$ | (2) $OCF_3$ | — |
| IIb-74 | H | $CH_2CH=CH_2$ | (2) Cl | — |
| IIb-75 | H | $CH_2CH=CH_2$ | (2) $OC_2H_5$ | — |
| IIb-76 | H | $CH_2CH=CH_2$ | (2) $CH_3$ | — |
| IIb-77 | H | $CH_2CH=CH_2$ | (2) Cl, (4) Cl | — |
| IIb-78 | H | $CH_2CH=CH_2$ | (2) Cl, (5) Cl | — |
| IIb-79 | H | $CH_2CH=CH_2$ | (2) $OCH_3$, (5) $OCH_3$ | — |
| IIb-80 | H | $CH_2CH=CH_2$ | (2) $CH_3$, (4) $CH_3$ | — |
| IIb-81 | H | $CH_2CH=CH_2$ | (2) $CH_3$, (5) $CH_3$ | — |
| IIb-82 | H | 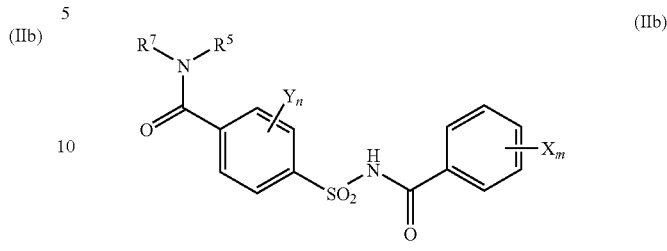 | (2) $OCH_3$ | — |
| IIb-83 | H | 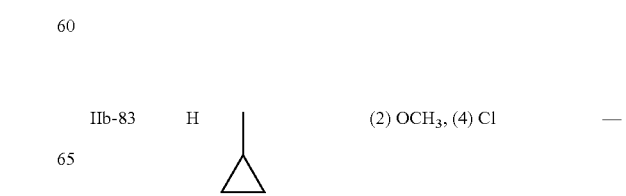 | (2) $OCH_3$, (4) Cl | — |

TABLE 2-continued

Examples of compounds of the formula (IIb)

(IIb)

| Ex. No. | R⁵ | R⁷ | (Position/s) X$_m$ | (Position/s) Y$_n$ |
|---|---|---|---|---|
| IIb-84 | H |  | (2) OCH$_3$, (4) CH$_3$ | — |
| IIb-85 | H |  | (2) OCH$_3$, (5) Cl | — |
| IIb-86 | H |  | (2) OCH$_3$, (4) Cl | — |
| IIb-87 | H |  | (2) OCH$_3$, (5) CH$_3$ | — |
| IIb-88 | H |  | (2) CF$_3$ | — |
| IIb-89 | H |  | (2) OCHF$_2$ | — |
| IIb-90 | H |  | (2) OCF$_3$ | — |
| IIb-91 | H |  | (2) Cl | — |
| IIb-92 | H |  | (2) OC$_2$H$_5$ | — |
| IIb-93 | H |  | (2) CH$_3$ | — |
| IIb-94 | H |  | (2) Cl, (4) Cl | — |
| IIb-95 | H |  | (2) Cl, (5) Cl | — |
| IIb-96 | H |  | (2) OCH$_3$, (5) OCH$_3$ | — |
| IIb-97 | H |  | (2) CH$_3$, (4) CH$_3$ | — |
| IIb-98 | H |  | (2) CH$_3$, (5) CH$_3$ | — |
| IIb-99 | H | C$_4$H$_9$-n | (2) OCH$_3$ | — |
| IIb-100 | H | C$_4$H$_9$-n | (2) OCH$_3$, (4) Cl | — |
| IIb-101 | H | C$_4$H$_9$-n | (2) OCH$_3$, (4) CH$_3$ | — |
| IIb-102 | H | C$_4$H$_9$-n | (2) OCH$_3$, (5) Cl | — |
| IIb-103 | H | C$_4$H$_9$-n | (2) OCH$_3$, (4) Cl | — |
| IIb-104 | H | C$_4$H$_9$-n | (2) OCH$_3$, (5) CH$_3$ | — |
| IIb-105 | H | C$_4$H$_9$-n | (2) CF$_3$ | — |
| IIb-106 | H | C$_4$H$_9$-n | (2) OCHF$_2$ | — |
| IIb-107 | H | C$_4$H$_9$-n | (2) OCF$_3$ | — |
| IIb-108 | H | C$_4$H$_9$-n | (2) Cl | — |
| IIb-109 | H | C$_4$H$_9$-n | (2) OC$_2$H$_5$ | — |
| IIb-110 | H | C$_4$H$_9$-n | (2) CH$_3$ | — |
| IIb-111 | H | C$_4$H$_9$-n | (2) Cl, (4) Cl | — |
| IIb-112 | H | C$_4$H$_9$-n | (2) Cl, (5) Cl | — |
| IIb-113 | H | C$_4$H$_9$-n | (2) OCH$_3$, (5) OCH$_3$ | — |
| IIb-114 | H | C$_4$H$_9$-n | (2) CH$_3$, (4) CH$_3$ | — |
| IIb-115 | H | C$_4$H$_9$-n | (2) CH$_3$, (5) CH$_3$ | — |
| IIb-116 | H | C$_4$H$_9$-i | (2) OCH$_3$ | — |
| IIb-117 | H | C$_4$H$_9$-i | (2) OCH$_3$, (4) Cl | — |
| IIb-118 | H | C$_4$H$_9$-i | (2) OCH$_3$, (4) CH$_3$ | — |
| IIb-119 | H | C$_4$H$_9$-i | (2) OCH$_3$, (5) Cl | — |
| IIb-120 | H | C$_4$H$_9$-i | (2) OCH$_3$, (4) Cl | — |
| IIb-121 | H | C$_4$H$_9$-i | (2) OCH$_3$, (5) CH$_3$ | — |
| IIb-122 | H | C$_4$H$_9$-i | (2) CF$_3$ | — |
| IIb-123 | H | C$_4$H$_9$-i | (2) OCHF$_2$ | — |
| IIb-124 | H | C$_4$H$_9$-i | (2) OCF$_3$ | — |
| IIb-125 | H | C$_4$H$_9$-i | (2) Cl | — |
| IIb-126 | H | C$_4$H$_9$-i | (2) OC$_2$H$_5$ | — |
| IIb-127 | H | C$_4$H$_9$-i | (2) CH$_3$ | — |
| IIb-128 | H | C$_4$H$_9$-i | (2) Cl, (4) Cl | — |
| IIb-129 | H | C$_4$H$_9$-i | (2) Cl, (5) Cl | — |
| IIb-130 | H | C$_4$H$_9$-i | (2) OCH$_3$, (5) OCH$_3$ | — |
| IIb-131 | H | C$_4$H$_9$-i | (2) CH$_3$, (4) CH$_3$ | — |
| IIb-132 | H | C$_4$H$_9$-i | (2) CH$_3$, (5) CH$_3$ | — |
| IIb-133 | H | C$_4$H$_9$-s | (2) OCH$_3$ | — |
| IIb-134 | H | C$_4$H$_9$-s | (2) OCH$_3$, (4) Cl | — |
| IIb-135 | H | C$_4$H$_9$-s | (2) OCH$_3$, (4) CH$_3$ | — |
| IIb-136 | H | C$_4$H$_9$-s | (2) OCH$_3$, (5) Cl | — |
| IIb-137 | H | C$_4$H$_9$-s | (2) OCH$_3$, (4) Cl | — |
| IIb-138 | H | C$_4$H$_9$-s | (2) OCH$_3$, (5) CH$_3$ | — |
| IIb-139 | H | C$_4$H$_9$-s | (2) CF$_3$ | — |
| IIb-140 | H | C$_4$H$_9$-s | (2) OCHF$_2$ | — |
| IIb-141 | H | C$_4$H$_9$-s | (2) OCF$_3$ | — |
| IIb-142 | H | C$_4$H$_9$-s | (2) Cl | — |
| IIb-143 | H | C$_4$H$_9$-s | (2) OC$_2$H$_5$ | — |
| IIb-144 | H | C$_4$H$_9$-s | (2) CH$_3$ | — |

TABLE 2-continued

Examples of compounds of the formula (IIb)

(IIb)

| Ex. No. | R⁵ | R⁷ | (Position/s) $X_m$ | (Position/s) $Y_n$ |
|---|---|---|---|---|
| IIb-145 | H | C₄H₉-s | (2) Cl, (4) Cl | — |
| IIb-146 | H | C₄H₉-s | (2) Cl, (5) Cl | — |
| IIb-147 | H | C₄H₉-s | (2) OCH₃, (5) OCH₃ | — |
| IIb-148 | H | C₄H₉-s | (2) CH₃, (4) CH₃ | — |
| IIb-149 | H | C₄H₉-s | (2) CH₃, (5) CH₃ | — |
| IIb-150 | H | CH₂CH₂OCH₃ | (2) OCH₃ | — |
| IIb-151 | H | CH₂CH₂OCH₃ | (2) OCH₃, (4) Cl | — |
| IIb-152 | H | CH₂CH₂OCH₃ | (2) OCH₃, (4) CH₃ | — |
| IIb-153 | H | CH₂CH₂OCH₃ | (2) OCH₃, (5) Cl | — |
| IIb-154 | H | CH₂CH₂OCH₃ | (2) OCH₃, (4) Cl | — |
| IIb-155 | H | CH₂CH₂OCH₃ | (2) OCH₃, (5) CH₃ | — |
| IIb-156 | H | CH₂CH₂OCH₃ | (2) CF₃ | — |
| IIb-157 | H | CH₂CH₂OCH₃ | (2) OCHF₂ | — |
| IIb-158 | H | CH₂CH₂OCH₃ | (2) OCF₃ | — |
| IIb-159 | H | CH₂CH₂OCH₃ | (2) Cl | — |
| IIb-160 | H | CH₂CH₂OCH₃ | (2) OC₂H₅ | — |
| IIb-161 | H | CH₂CH₂OCH₃ | (2) CH₃ | — |
| IIb-162 | H | CH₂CH₂OCH₃ | (2) Cl, (4) Cl | — |
| IIb-163 | H | CH₂CH₂OCH₃ | (2) Cl, (5) Cl | — |
| IIb-164 | H | CH₂CH₂OCH₃ | (2) OCH₃, (5) OCH₃ | — |
| IIb-165 | H | CH₂CH₂OCH₃ | (2) CH₃, (4) CH₃ | — |
| IIb-166 | H | CH₂CH₂OCH₃ | (2) CH₃, (5) CH₃ | — |
| IIb-167 | H | CH₂C≡CH | (2) OCH₃ | — |
| IIb-168 | H | CH₂C≡CH | (2) OCH₃, (4) Cl | — |
| IIb-169 | H | CH₂C≡CH | (2) OCH₃, (4) CH₃ | — |
| IIb-170 | H | CH₂C≡CH | (2) OCH₃, (5) Cl | — |
| IIb-171 | H | CH₂C≡CH | (2) OCH₃, (4) Cl | — |
| IIb-172 | H | CH₂C≡CH | (2) OCH₃, (5) CH₃ | — |
| IIb-173 | H | CH₂C≡CH | (2) CF₃ | — |
| IIb-174 | H | CH₂C≡CH | (2) OCHF₂ | — |
| IIb-175 | H | CH₂C≡CH | (2) OCF₃ | — |
| IIb-176 | H | CH₂C≡CH | (2) Cl | — |
| IIb-177 | H | CH₂C≡CH | (2) OC₂H₅ | — |
| IIb-178 | H | CH₂C≡CH | (2) CH₃ | — |
| IIb-179 | H | CH₂C≡CH | (2) Cl, (4) Cl | — |
| IIb-180 | H | CH₂C≡CH | (2) Cl, (5) Cl | — |
| IIb-181 | H | CH₂C≡CH | (2) OCH₃, (5) OCH₃ | — |
| IIb-182 | H | CH₂C≡CH | (2) CH₃, (4) CH₃ | — |
| IIb-183 | H | CH₂C≡CH | (2) CH₃, (5) CH₃ | — |
| IIb-184 | H | CH₂CH₂OC₂H₅ | (2) OCH₃ | — |
| IIb-185 | H | CH₂CH₂OC₂H₅ | (2) OCH₃, (4) Cl | — |
| IIb-186 | H | CH₂CH₂OC₂H₅ | (2) OCH₃, (4) CH₃ | — |
| IIb-187 | H | CH₂CH₂OC₂H₅ | (2) OCH₃, (5) Cl | — |
| IIb-188 | H | CH₂CH₂OC₂H₅ | (2) OCH₃, (4) Cl | — |
| IIb-189 | H | CH₂CH₂OC₂H₅ | (2) OCH₃, (5) CH₃ | — |
| IIb-190 | H | CH₂CH₂OC₂H₅ | (2) CF₃ | — |
| IIb-191 | H | CH₂CH₂OC₂H₅ | (2) OCHF₂ | — |
| IIb-192 | H | CH₂CH₂OC₂H₅ | (2) OCF₃ | — |
| IIb-193 | H | CH₂CH₂OC₂H₅ | (2) Cl | — |
| IIb-194 | H | CH₂CH₂OC₂H₅ | (2) OC₂H₅ | — |
| IIb-195 | H | CH₂CH₂OC₂H₅ | (2) CH₃ | — |
| IIb-196 | H | CH₂CH₂OC₂H₅ | (2) Cl, (4) Cl | — |
| IIb-197 | H | CH₂CH₂OC₂H₅ | (2) Cl, (5) Cl | — |
| IIb-198 | H | CH₂CH₂OC₂H₅ | (2) OCH₃, (5) OCH₃ | — |
| IIb-199 | H | CH₂CH₂OC₂H₅ | (2) CH₃, (4) CH₃ | — |
| IIb-200 | H | CH₂CH₂OC₂H₅ | (2) CH₃, (5) CH₃ | — |

TABLE 2-continued

Examples of compounds of the formula (IIb)

(IIb)

R⁷–N(R⁵)–C(O)–[phenyl-Y_n]–SO₂–NH–C(O)–[phenyl-X_m]

| Ex. No. | R⁵ | R⁷ | (Position/s) X_m | (Position/s) Y_n |
|---|---|---|---|---|
| IIb-201 | CH₃ | CH₃ | (2) OCH₃ | — |
| IIb-202 | CH₃ | CH₃ | (2) OCH₃, (4) Cl | — |
| IIb-203 | CH₃ | CH₃ | (2) OCH₃, (4) CH₃ | — |
| IIb-204 | CH₃ | CH₃ | (2) OCH₃, (5) Cl | — |
| IIb-205 | CH₃ | CH₃ | (2) OCH₃, (4) Cl | — |
| IIb-206 | CH₃ | CH₃ | (2) OCH₃, (5) CH₃ | — |
| IIb-207 | CH₃ | CH₃ | (2) CF₃ | — |
| IIb-208 | CH₃ | CH₃ | (2) OCHF₂ | — |
| IIb-209 | CH₃ | CH₃ | (2) OCF₃ | — |
| IIb-210 | CH₃ | CH₃ | (2) Cl | — |
| IIb-211 | CH₃ | CH₃ | (2) OC₂H₅ | — |
| IIb-212 | CH₃ | CH₃ | (2) CH₃ | — |
| IIb-213 | CH₃ | CH₃ | (2) Cl, (4) Cl | — |
| IIb-214 | CH₃ | CH₃ | (2) Cl, (5) Cl | — |
| IIb-215 | CH₃ | CH₃ | (2) OCH₃, (5) OCH₃ | — |
| IIb-216 | CH₃ | CH₃ | (2) CH₃, (4) CH₃ | — |
| IIb-217 | CH₃ | CH₃ | (2) CH₃, (5) CH₃ | — |
| IIb-218 | C₂H₅ | C₂H₅ | (2) OCH₃ | — |
| IIb-219 | C₂H₅ | C₂H₅ | (2) OCH₃, (4) Cl | — |
| IIb-220 | C₂H₅ | C₂H₅ | (2) OCH₃, (4) CH₃ | — |
| IIb-221 | C₂H₅ | C₂H₅ | (2) OCH₃, (5) Cl | — |
| IIb-222 | C₂H₅ | C₂H₅ | (2) OCH₃, (4) Cl | — |
| IIb-223 | C₂H₅ | C₂H₅ | (2) OCH₃, (5) CH₃ | — |
| IIb-224 | C₂H₅ | C₂H₅ | (2) CF₃ | — |
| IIb-225 | C₂H₅ | C₂H₅ | (2) OCHF₂ | — |
| IIb-226 | C₂H₅ | C₂H₅ | (2) OCF₃ | — |
| IIb-227 | C₂H₅ | C₂H₅ | (2) Cl | — |
| IIb-228 | C₂H₅ | C₂H₅ | (2) OC₂H₅ | — |
| IIb-229 | C₂H₅ | C₂H₅ | (2) CH₃ | — |
| IIb-230 | C₂H₅ | C₂H₅ | (2) Cl, (4) Cl | — |
| IIb-231 | C₂H₅ | C₂H₅ | (2) Cl, (5) Cl | — |
| IIb-232 | C₂H₅ | C₂H₅ | (2) OCH₃, (5) OCH₃ | — |
| IIb-233 | C₂H₅ | C₂H₅ | (2) CH₃, (4) CH₃ | — |
| IIb-234 | C₂H₅ | C₂H₅ | (2) CH₃, (5) CH₃ | — |

The compounds of the general formula (II) are known and/or can be prepared by processes known per se (cf. WO-A-97/45016/U.S. Pat. No. 6,235,680; WO-A-99/66795/U.S. Pat. No. 6,251,827; WO-A-99/16744).

Examples of the selective herbicidal combinations according to the invention of in each case one active compound of the general formula (I) and in each case one safener of the general formula (II) which are given particular emphasis are:

Active compound (I-1)—propoxycarbazone—in combination with the safeners listed in Table 1, in particular (IIa-13) to (IIa-56), (IIa-101) to (IIa-168) and (IIa-186) to (IIa-304), in particular IIa-101.

Active compound (I-1-Na salt)—propoxycarbazone-sodium—in combination with the safeners listed in Table 1, in particular (IIa-13) to (IIa-56), (IIa-101) to (IIa-168) and (IIa-186) to (IIa-304), in particular IIa-101.

Active compound (I-2)—flucarbazone—in combination with the safeners listed in Table 1, in particular (IIa-13) to (IIa-56), (IIa-101) to (IIa-168) and (IIa-186) to (IIa-304), in particular IIa-101.

Active compound (I-2-Na salt)—flucarbazone-sodium—in combination with the safeners listed in Table 1, in particular (IIa-13) to (IIa-56), (IIa-101) to (IIa-168) and (IIa-186) to (IIa-304), in particular IIa-101.

Active compound (I-1)—propoxycarbazone—in combination with the safeners listed in Table 2, in particular (IIb-14) to (IIb-98), (IIb-150) to (IIb-234).

Active compound (I-1-Na salt)—propoxycarbazone-sodium—in combination with the safeners listed in Table 2, in particular (IIb-14) to (IIb-98), (IIb-150) to (IIb-234).

Active compound (I-2)—flucarbazone—in combination with the safeners listed in Table 2, in particular (IIb-14) to (IIb-98), (IIb-150) to (IIb-234).

Active compound (I-2-Na salt)—flucarbazone-sodium—in combination with the safeners listed in Table 2, in particular (IIb-14) to (IIb-98), (IIb-150) to (IIb-234).

Surprisingly, it has now been found that the active compound combinations defined above of substituted arylsulphonylaminocarbonyl-triazolinones of the general formula (I) and safeners (antidotes) of the general formula (II), whilst being highly compatible with crop plants, have a particularly high herbicidal activity and can be used in various crops, in particular cereals (especially barley and wheat), but also maize and rice, for the selective control of weeds.

Here, it has to be considered to be surprising that, from a large number of known safeners or antidotes which are capable of antagonizing the damaging effect of a herbicide on the crop plants, it is in particular the compounds of the formula (II) listed above which neutralize the damaging effect of substituted arylsulphonylaminocarbonyl-triazolinones on the crop plants virtually completely without negatively affecting the herbicidal activity with respect to the weeds.

Emphasis is given here to the particularly advantageous effect of the particularly and most preferred combination partners from the general formula (II), in particular in respect of sparing cereal plants, such as, for example, wheat, barley and rye, but also maize and rice, as crop plants.

The active compound combinations according to the invention can be used, for example, in connection with the following plants:

Dicotyledonous weeds of the genera: *Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus, Taraxacum.*

Dicotyledonous crops of the genera: *Gossypium, Glycine, Beta, Daucus, Phaseolus, Pisum, Solanum, Linum, Ipomoea, Vicia, Nicotiana, Lycopersicon, Arachis, Brassica, Lactuca, Cucumis, Cuburbita, Helianthus.*

Monocotyledonous weeds of the genera: *Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus, Apera.*

Monocotyledonous crops of the genera: *Oryza, Zea, Triticum, Hordeum, Avena, Secale, Sorghum, Panicum, Saccharum, Ananas, Asparagus, Allium.*

However, the use of the active compound combinations according to the invention is in no way restricted to these genera, but also extends in the same manner to other plants. According to the invention, crop plants are all plants and plant varieties including transgenic plants and plant varieties, where on transgenic plants and plant varieties it is also possible for synergistic effects to occur.

The advantageous effect of the crop plant compatibility of the active compound combinations according to the invention is particularly highly pronounced at certain concentration ratios. However, the weight ratios of the active compounds in the active compound concentrations can be varied within relatively wide ranges. In general, 0.001 to 1000 parts by weight, preferably 0.01 to 100 parts by weight, and particularly preferably 0.1 to 10 parts by weight of one of the compounds which improve crop plant compatibility mentioned under (b) above (antidotes/safeners) are present per part by weight of active compound of the formula (I) or its salts.

The active compounds or active compound combinations can be converted into the customary formulations, such as solutions, emulsions, wettable powders, suspensions, powders, dusting agents, pastes, soluble powders, granules, suspoemulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers.

If the extender used is water, it is also possible to use, for example, organic solvents as auxiliary solvents. Suitable liquid solvents are essentially: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulfoxide, and also water.

Suitable solid carriers are:

for example ammonium salts and ground natural minerals, such as kaolins, clays, talc, chalk, quartz, attapulgite, montmorillonite or diatomaceous earth, ground synthetic minerals, such as finely divided silica, alumina and silicates, suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifiers and/or foam-formers are: for example non-ionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates and protein hydrolyzates; suitable dispersants are: for example lignosulfite waste liquors and methylcellulose.

Tackifiers such as carboxymethylcellulose and natural and synthetic polymers in the form of powders, granules or latices, such as gum arabic, polyvinyl alcohol and polyvinyl acetate, and also natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations generally comprise from 0.1 to 95 percent by weight of active compounds including the safeners, preferably between 0.5 and 90%.

The active compound combinations according to the invention are generally used in the form of finished formulations. However, the active compounds contained in the active compound combinations can also be mixed in individual formulations when used, i.e. in the form of tank mixes.

The novel active compound combinations, as such or in their formulations, can furthermore be used as a mixture with other known herbicides, finished formulations or tank mixes again being possible. A mixture with other known active compounds, such as fungicides, insecticides, acaricides, nematicides, bird repellents, growth factors, plant nutrients and agents which improve soil structure, is also possible. For certain intended uses, in particular in the post-emergence method, it may furthermore be advantageous to include, as further additives in the formulations, mineral or vegetable oils which are tolerated by plants (for example the commercial preparation "Rako Binol"), or ammonium salts such as, for example, ammonium sulphate or ammonium thiocyanate.

The novel active compound combinations can be used as such, in the form of their formulations or the use forms prepared therefrom by further dilution, such as ready-to-use solutions, suspensions, emulsions, powders, pastes and granules. They are used in the customary manner, for example by washing, spraying, atomizing, dusting or scattering.

The amounts of the active compound combinations according to the invention applied can be varied within a certain range; they depend, inter alia, on the weather and on soil factors. In general, the application rates are between 0.005 and 5 kg per ha, preferably between 0.01 and 2 kg per ha, particularly preferably between 0.05 and 1.0 kg per ha.

The active compound combinations according to the invention can be applied before and after emergence of the plants, that is to say by the pre-emergence and post-emergence method.

USE EXAMPLES

The active compound (flucarbazone-sodium and propoxycarbazone-sodium were each used as WG 70) or safener components are in each case dissolved in a few ml (generally 2-3 ml) of solvent (generally acetone or N,N-dimethyl-formamide), and the solutions are combined and then—if appropriate after addition of an emulsifier—diluted with water to the desired concentration. In general, an aqueous spray liquor was prepared using 0.5% of the additive Renex-36.

Example A

Post-Emergence Test

The test plants are grown under controlled conditions (temperature, light, atmospheric humidity) in a greenhouse. The test plants are sprayed when they have reached a height of 5-15 cm. The concentration of the spray liquor is chosen such that the particular amounts of active compound desired are applied in 500 l of water/ha.

After spraying, the pots with the test plants are kept in a greenhouse chamber under controlled conditions (temperature, light, atmospheric humidity) until the test has ended.

About three weeks after the application, the degree of damage to the crop plants is rated in % damage in comparison to the development of the untreated control.

The figures denote:

0%=no damage (like untreated control)

100%=total destruction/damage

Active compounds, application rates, test plants and results are shown in the tables below, the terms being used in the tables being as defined below:

a.i.=active ingredient=active compound/safener

Ex. No. IIa-101=

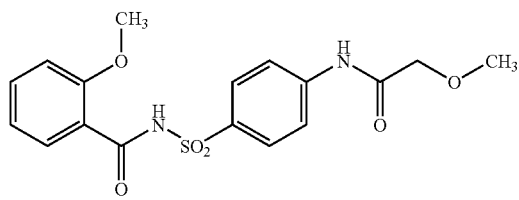

TABLE A1

Post emergence test/greenhouse

| Active compound (+safener) | Application rate (g of a.i./ha) | Damage Winter barley (in %) |
|---|---|---|
| propoxycarbazone-sodium | 4 | 60 |
|  | 2 | 35 |
| propoxycarbazone-sodium + Ex. No. IIa-101 | 4 + 100 | 40 |
|  | 2 + 100 | 25 |

TABLE A2

Post emergence test/greenhouse

| Active compound (+safener) | Application rate (g of a.i./ha) | Damage Winter barley (in %) |
|---|---|---|
| flucarbazone-sodium | 8 | 40 |
| flucarbazone-sodium + Ex. No. IIa-101 | 8 + 100 | 20 |

TABLE A1

Post emergence test/greenhouse

| Safener | Application rate (g of a.i./ha) | Damage Winter barley (in %) |
|---|---|---|
| Ex. No. IIa-101 | 100 | 0 |
|  | 30 | 0 |

What is claimed is:

1. A composition comprising an effective amount of an active compound combination comprising (a) 2-(2-methoxycarbonyl-phenylsulphonylaminocarbonyl)-4-methyl-5-n-propoxy-2,4-dihydro-3H-1,2,4-triazol-3-one (propoxycarbazone) or the corresponding sodium salt (propoxycarbazone-sodium)

and (b) N-[4-(cyclopropylcarbamoyl)phenylsulfonyl]-2-methoxybenzamide.

2. A method for controlling undesirable plants comprising allowing an effective amount of a composition according to claim 1 to act on undesirable plants and/or their habitat.

3. A process for preparing a herbicidal composition comprising mixing a composition according to claim 1 with one or more surfactants and/or extenders.

* * * * *

UNITED STATES PATENT AND TRADEMARK OFFICE
CERTIFICATE OF CORRECTION

PATENT NO.       : 7,615,514 B2                                          Page 1 of 1
APPLICATION NO.  : 10/488037
DATED            : November 10, 2009
INVENTOR(S)      : Feucht et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 196 days.

Signed and Sealed this

Nineteenth Day of October, 2010

David J. Kappos
*Director of the United States Patent and Trademark Office*